United States Patent [19]
Willson

[11] Patent Number: 5,134,484
[45] Date of Patent: Jul. 28, 1992

[54] SUPERIMPOSING METHOD AND APPARATUS USEFUL FOR SUBLIMINAL MESSAGES

[75] Inventor: Joseph Willson, Newtown Square, Pa.

[73] Assignee: MindsEye Educational Systems, Inc., Strafford, Pa.

[21] Appl. No.: 359,974

[22] Filed: Jun. 1, 1989

[51] Int. Cl.[5] .................... H04N 5/272; H04N 5/45
[52] U.S. Cl. .................................. 358/183; 358/160
[58] Field of Search .................... 358/22, 183, 160

[56] References Cited

U.S. PATENT DOCUMENTS

| | | | |
|---|---|---|---|
| 4,616,261 | 10/1986 | Crawford | 358/183 |
| 4,644,399 | 2/1987 | McCord et al. | 358/142 |
| 4,675,737 | 6/1987 | Fujino et al. | 358/183 |
| 4,748,504 | 5/1988 | Ikeda et al. | 358/183 X |
| 4,777,529 | 10/1988 | Schultz et al. | 358/142 X |
| 4,855,827 | 8/1989 | Best | 358/142 X |
| 4,864,399 | 9/1989 | Romesburg et al. | 358/148 |
| 4,891,705 | 1/1990 | Suzuki et al. | 358/22 X |
| 4,899,139 | 2/1990 | Ishimochi | 358/183 X |
| 4,907,086 | 3/1990 | Truong | 358/183 |

*Primary Examiner*—James J. Groody
*Assistant Examiner*—Mark R. Powell
*Attorney, Agent, or Firm*—Louis Weinstein

[57] ABSTRACT

Data to be displayed is combined with a composite video signal. The data is stored in a memory in digital form. Each byte of the data is read out in sequential fashion to determine: the recurrence display rate of the data according to the frame sync pulses of the video signal; the location of the data within the video image according to the line sync pulses of the video signal; and the location of the data display within the video image according to the position information. Synchronization of the data with the video image is derived from the sync pulses of the composite video signal. A similar technique is employed to combine sound data with an audio signal. Data to be displayed may be presented as a subliminal message or may persist for a given time interval. The data may be derived from a variety of sources including a prerecorded or live video signal. The message may be a reminder message displayed upon a television screen to remind the viewer of an appointment. The data may be stored in a variety of different memory devices capable of high speed data retrieval. The data may be generated locally on-line or off-line and transferred to memory which stores the data necessary to create the message.

109 Claims, 18 Drawing Sheets

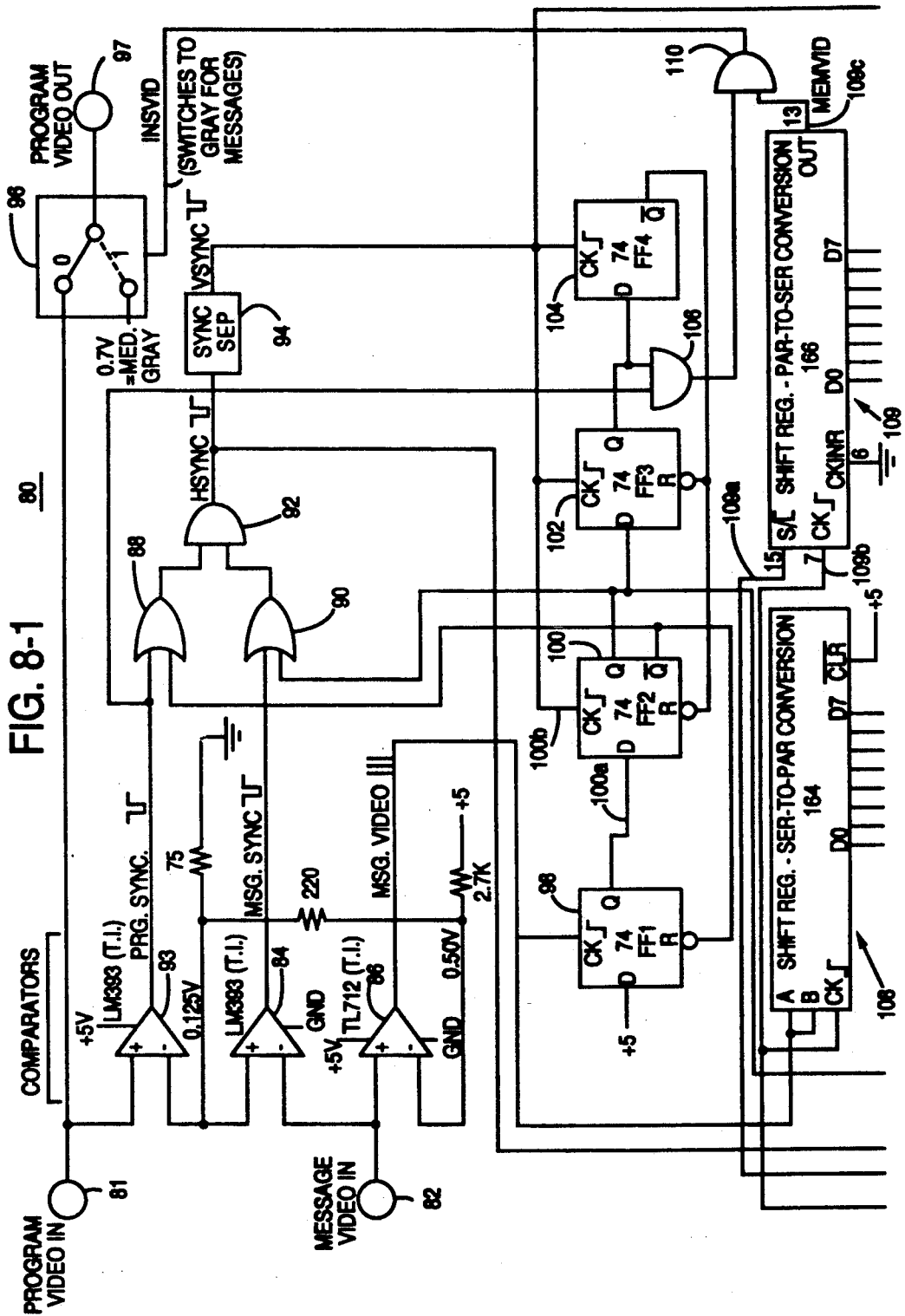

SUPERIMPOSING METHOD AND APPARATUS USEFUL FOR SUBLIMINAL MESSAGES

FIELD OF THE INVENTION

The present invention relates to apparatus for combining video signals with additional information, and more particularly to a novel method and apparatus for superimposing messages, graphic information and the like to video signals and/or audio signals and which is uniquely adapted to provide both static and dynamic information for either normal or subliminal presentation.

BACKGROUND OF THE INVENTION

A variety of different applications exist wherein it is desirable to combine information signals. For example, one typical application is the provision of subliminal messages. In order to present a subliminal message upon a television screen, it is necessary to provide apparatus for producing the data in the form of signals which are capable of being processed by a standard television receiver and to synchronize the signals with the R.F. signals being broadcast to the television receiver such as, for example, a transmission from a local or network television station to a television in a viewer's residence.

The transmitted video signal is typically comprised of synchronizing signals, namely, frame and line synchronizing signals also referred to as vertical and horizontal sync signals, respectively. The sync signals are combined with the image information to form a composite video signal which is transmitted to a television receiver by way of a carrier frequency signal which is modulated by the composite video signal.

The modulated carrier is processed at the television receiver to remove the composite video signal from the carrier frequency signal whereupon the video display is generated in accordance with the information signals and the corresponding synchronizing signals.

Heretofore, conventional techniques for displaying information such as messages, graphic and pictorial images and the like, utilize synchronizing signals which are generated specifically for the data to be superimposed, which signals are generated totally independently of the synchronizing signals forming part of the composite video signal.

One such conventional prior art technique is described in U.S. Pat. No. 4,616,261 in which switching means is provided for alternately switching between the composite video signal and the information to be combined therewith. This system has the disadvantages of cutting out the composite video signal during the time that the message, such as a subliminal message, is being introduced, and further requires separate, independent sync signals for the subliminal message, which switching system is thus incapable of precisely synchronizing the subliminal message with the video image as regards its rate of occurrence and precise location upon the screen.

BRIEF DESCRIPTION OF THE INVENTION

The present invention is characterized by comprising a system in which the synchronizing signals for the overlay message are derived from the composite video signal, thus assuring perfect synchronism of the overlay message with the video image and further assuring the precise location of the overlay message according to the desires of the particular application. An overlay message (or messages) may be a subliminal or a persistent image or combinations thereof.

The present invention is characterized by comprising an electronic solid state system in which a memory source which may, for example, be a READ ONLY MEMORY (ROM) contains information relating to the refresh rate, the line position and the location on each line at which the message is to be displayed, as well as information representing the message.

The present invention is characterized by comprising a method and apparatus for extracting a composite video signal from a modulated carrier, extracting the frame and line signals from the composite video signal, examining a memory device in which data representing the frame count, line count and placement information are stored in a predetermined arrangement within the memory whereby a frame count is utilized to initiate the regeneration of message signals and to determine the refresh rate therefor, a line count is utilized to determine the line or lines which are to receive information and the position information is utilized to determine the location of the display data on each line of the video image, as well as the arrangement of the data or message on each line. The line (i.e., line sync pulse) count is extracted from memory and compared with the count of accumulated line sync pulses derived from the composite video signal. When the number of line sync pulses accumulated compares with (i.e. is equal to) the line count extracted from the memory, the line position count is then extracted from memory and the pulses generated by a timing pulse generator are counted and the count of the line position is compared with the timing pulses accumulated from the timing pulse generator. When these two counts compare, the data in the next memory location is extracted, which data represents the display information, and may be in the form of the presence or absence of a dot or the presence or absence of a dot of a predetermined brightness. For each location along the line which is to contain a dot, a dot production signal is combined with the composite video signal to produce a composite video plus message signal which is then preferably modulated with the channel 3 or channel 4 carrier, for example, for coupling to the television receiver for presentation of the video image and overlay message information upon the television screen, which may be a subliminal and/or a persistent message.

Each line making up the television display, which may, for example, be a 525 line screen, is divided into a precise number of data (i.e. dot) positions according to a precision timing pulse generator. The timing pulse generator generates pulses at a rate to precisely create the number of data positions per line, and which is the same for each line. The accuracy of the timing pulse generator is enhanced by automatically restarting the timing pulse generator each time a line sync signal is produced to assure initiation of the first timing pulse with a line sync signal and further to assure that the precise number of pulses are produced for each line making up the video display. Thus, the data on each line is precisely located relative to the left-hand edge of the display screen, for example.

The information to be displayed per line may necessitate a storage capacity of one or a plurality of binary bytes. The bytes are sequentially withdrawn from the memory, which is preferably a READ ONLY MEM- ORY (ROM), to determine the number of data positions or dots to be "painted" on each line.

When the desired number of dots have been "painted" for a given line, the next byte extracted from memory contains an instruction code which causes the system to wait for the next line sync pulse whereupon the number of bytes necessary to represent the dots to be painted on the next horizontal line are likewise extracted in sequential fashion.

When all of the dots to be painted to complete an image have been combined with the composite video signal, the next byte extracted from memory is a reset code whereby the system is caused to return to the first byte in the memory for the message program. The refresh rate is determined by counting the frame sync pulses and comparing the count against the frame count stored in memory. The frame sync pulse count thus determines the refresh rate, i.e., the rate at which the data is refreshed. The data may be a message, a graphic presentation of either a static or dynamic nature or a combination thereof. The data may be audio in nature as will be described.

In one preferred embodiment, the dots which are "painted" on each line may have a uniform brightness (i.e., presence or absence of a dot of a fixed brightness or illumination level).

Alternatively, each dot may have a brightness level lying within a predetermined range whereby the brightness level for each dot is determined by binary coded data which is converted by means of a digital-to-analog converter to generate a dot of brightness determined by the digital value stored for that dot whose analog value (represented in digital form) falls within a range between a minimum and a maximum brightness. In either case, the dot signal is additive to the composite video signal, always increasing (i.e., never decreasing) the brightness level of the image created by the composite video signal.

Another alternative technique is to create a fixed gray level at the location of each "dot" in place of adding a level to the video signal.

As still another alternative embodiment, the present invention may be utilized to introduce a subliminal audio message to an audio signal. The audio signal may, for example, be recorded on an audio cassette tape or may be broadcast from a remote radio or television transmitter. Upon initiation of tape play or receipt of an RF carrier, a timing pulse generator is activated. A memory is examined to extract the first byte of information representing the refresh rate of the audio message which is refreshed at a rate determined by the count value stored in the binary byte. This count is compared with pulses developed by a timing pulse generator so that, when the accumulated pulses compare with the stored count, the next byte (a message byte) is extracted from memory. The message bytes represent, in binary format, an instantaneous portion of the audio (analog) signal. Each digital value is converted into an analog value and is then combined with the audio signal. The memory stores a number of bytes sufficient to represent each word or sound.

Bytes may also be provided in memory for providing dead intervals between adjacent words or sound, where appropriate.

If desired, the audio signal may be in the form of an AM or FM signal received from a remote transmitter and comprised of a carrier modulated by the audio signal according to either an AM or FM technique. The carrier may be demodulated whereupon the subliminal message, once converted into analog form, is combined with the audio signal whereupon the combined signals may then be used to modulate the carrier frequency for playback by the AM (or FM) tuner.

If desired, the subliminal message may be an audio message superimposed upon the television message. If desired, the audio message may be generated in synchronism with the video (subliminal) message. As an alternative, the audio (subliminal) message may be generated utilizing the refresh rate information employed for generating a subliminal video message. The method and apparatus of the present invention may be utilized to provide an appointment or reminder capability by superimposing a reminder message upon the television display to remind the observer of an appointment, for example, the message data to be superimposed on the video image being stored in memory and comprised of data and instructions similar to those employed for providing a subliminal or persistent image.

The data to be superimposed may be derived from a variety of sources such as a live television broadcast source, a video composite signal stored in video casette tape or a laser disc or other off-line memories. The data may be generated through the keyboard of a computer, stored in the computer memory and transferred to the memory employed in the apparatus of the present invention, the last-mentioned memory preferably being any memory capable of high speed data storage and retrieval such as ROMs, RAMs, diskettes, laser discs, bubble memories and other like devices.

The system of the present invention is capable of creating an image for one or more fields such as one field or both fields of a frame comprised of two interlaced fields or a succession of fields in cases where a persistent image is desired. This capability is obtained by storing the address of the date to be repeated in a register and returning to the stored address at a rate determined by a count stored in a repetition counter and which is derived from a repeat segment byte stored in memory and comprised of a repeat segment instruction code and a repetition valve.

The subliminal message may be preceded by an introductory frame which may include the title of the message to be presented, the company name and/or logo, or the like. Since it is desired that the introductory frame persist for an interval of at least several seconds, a technique is provided for successively repeating the field of the introductory image a predetermined number of times by initiating an introductory mode and triggering the field counter to repeat the bytes making up the field for a predetermined number of successive frame sync pulses and terminating the introductory mode when the field counter reaches a predetermined count.

OBJECTS OF THE INVENTION

Brief Description of the Figures

It is one object of the present invention to provide novel method and apparatus for generating data and for combining said data with a standard audio and/or video communication.

Still another object of the present invention is to generate data for combination with an audio and/or video communication in which the data is synchronized in accordance with the synchronizing signals forming an integral part of the composite video and/or audio signal.

Figure 1:
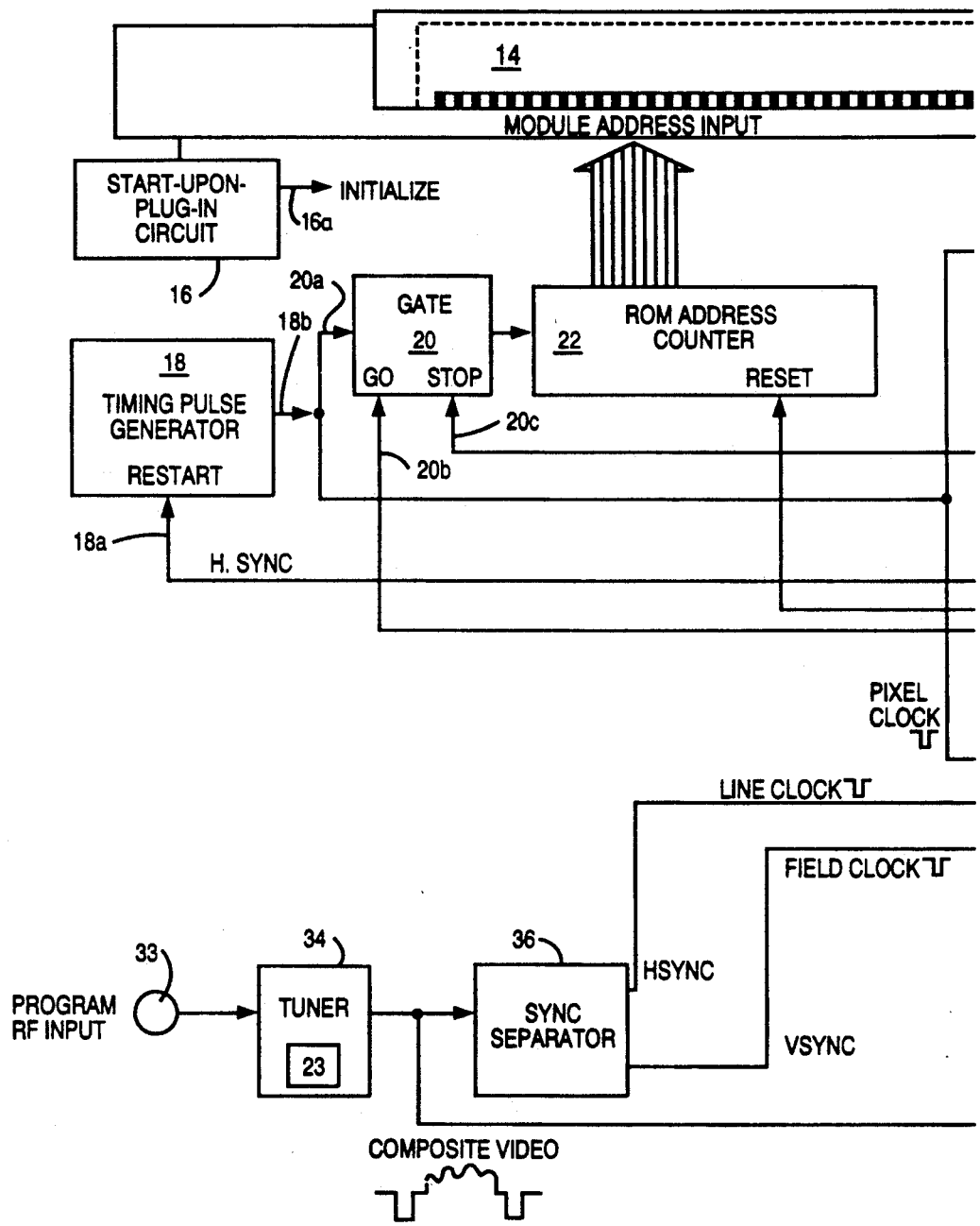

Still another object of the present invention is to provide a novel method and apparatus for generating audio and/or video data stored in a readable memory in digital fashion.

Still another object of the present invention is to provide a novel method and apparatus for generating audio and/or video data for combining with audio and/or video signals, which data may be varied by releasable insertion of a selected memory device in which all of the information is stored in digital fashion and wherein the data is altered simply by removal of one memory device and replacement with another.

Still another object of the present invention is to provide means for accurately synchronizing displayable data with a video display, for example, wherein timing signals are generated in synchronism with composite video timing signals by the provision of a timing pulse generator which is automatically restarted upon the occurrence of each successive timing signal to obtain accurate synchronization.

Still another object of the present invention is to provide a novel method and apparatus for generating data in synchronism with a video display created by composite video signals wherein the refresh rate, location of the data on the display screen and the data contents are stored in a memory device in a digital format.

Still another object of the present invention is to provide a novel method and apparatus for generating data for synchronous combination with composite video signals and the like wherein stored data in a memory is successively accessed to create a signal for combination with the composite video signal.

Still another object of the present invention is to provide a novel data compression method and apparatus for reducing the number of binary words required to represent the data to be combined with audio or video signal by an instruction which provides for the repetition of a continuous string of bits of the same signal level according to a count stored in a memory which controls the number of successive repetitions of the continuous string.

Still another object of the present invention is to provide a novel method and apparatus for controlling the persistence of one segment of a message to be superimposed upon a video signal by successively retrieving the stored data representing the message segment to be repeated under the control of a message repeat instruction stored in memory.

Still another object of the present invention is to provide a novel method and apparatus for superimposing first and second video signals by converting the video signal of one frame of image data of one of said video signals into a string of pulses and sequentially combining the string of pulses with the other video signal employing the sync signals of the latter video signal for synchronization.

Still another object of the present invention is to provide a novel method and apparatus for superimposing a video signal with message data where the message data is presented in a signal format similar to the video signal wherein the data is converted into a string of pulses and sequentially combined with the video signal whose sync signals are used as the basis for synchronizing the string of pulses and the video signal.

Figures 1, 2:
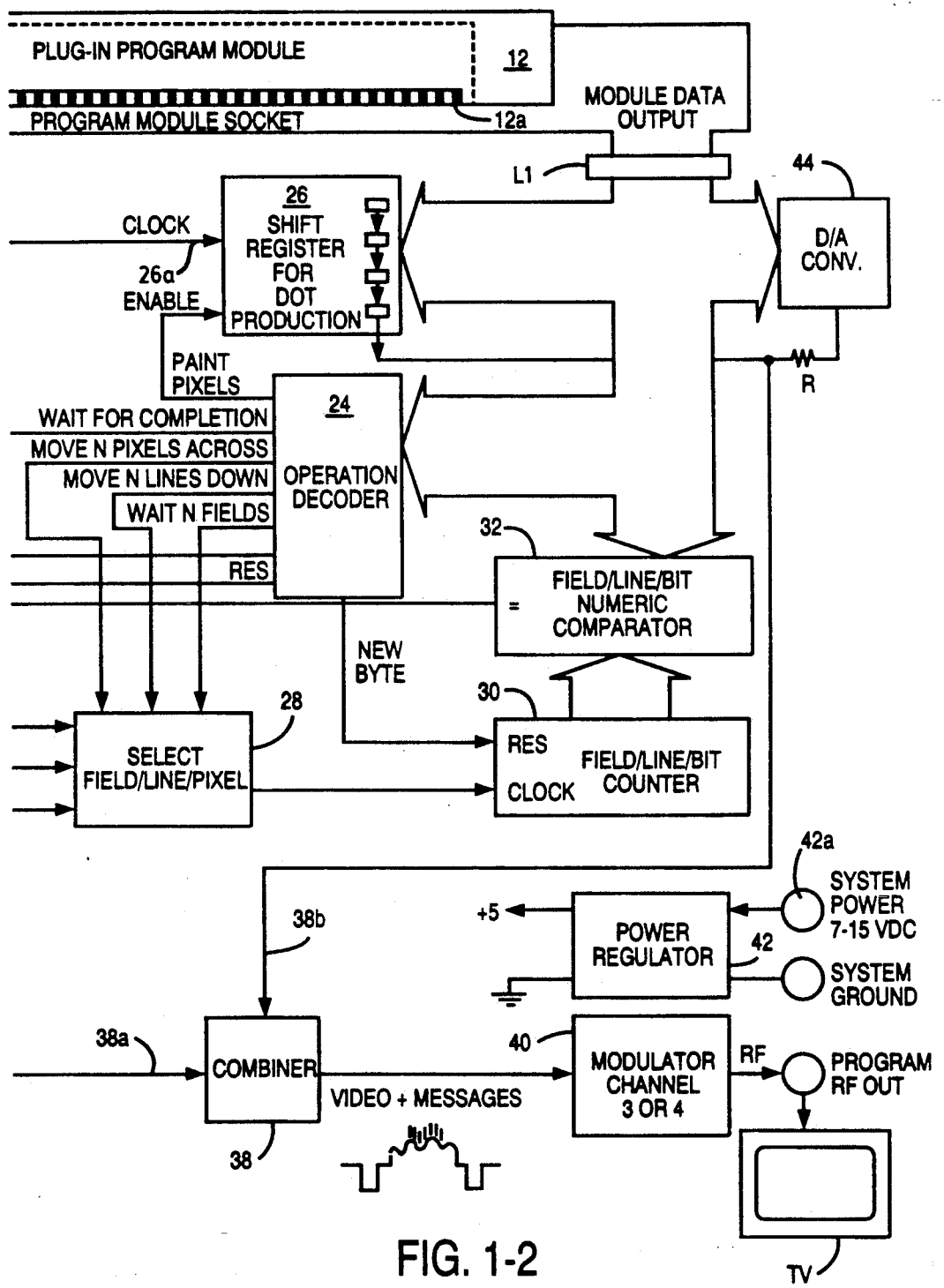
Figures 1, 2:
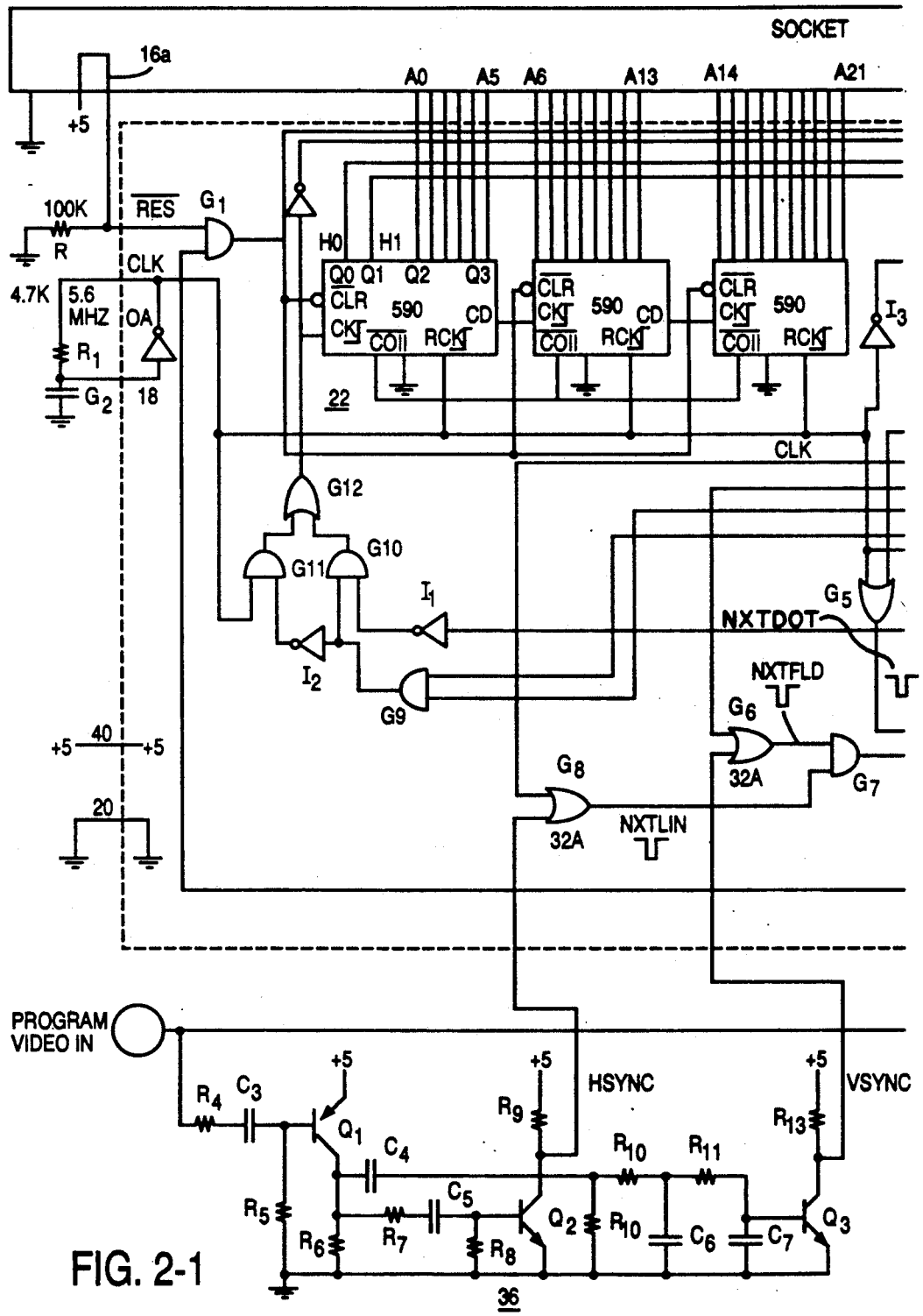
Figure 2:
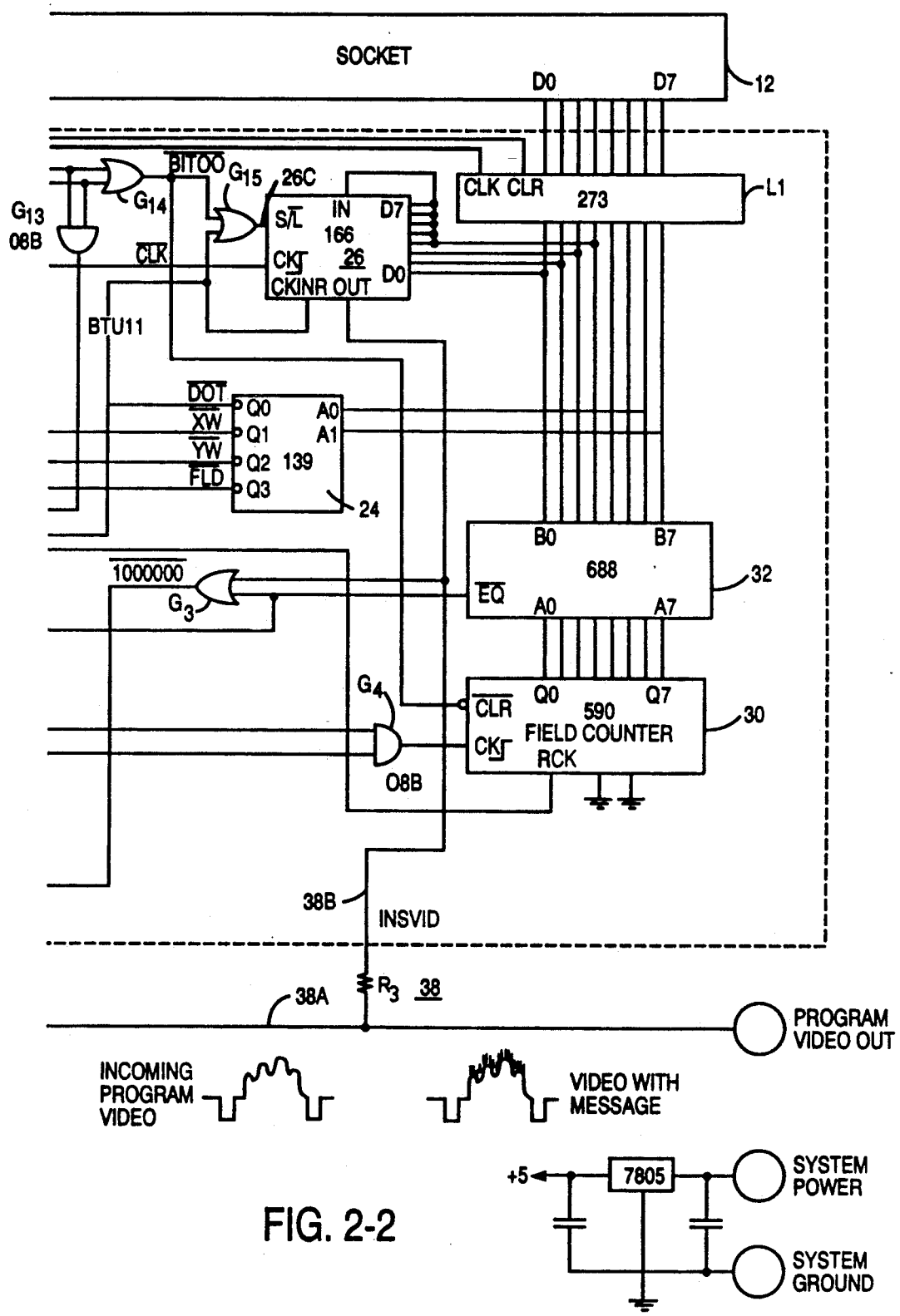
Figures 1, 6:
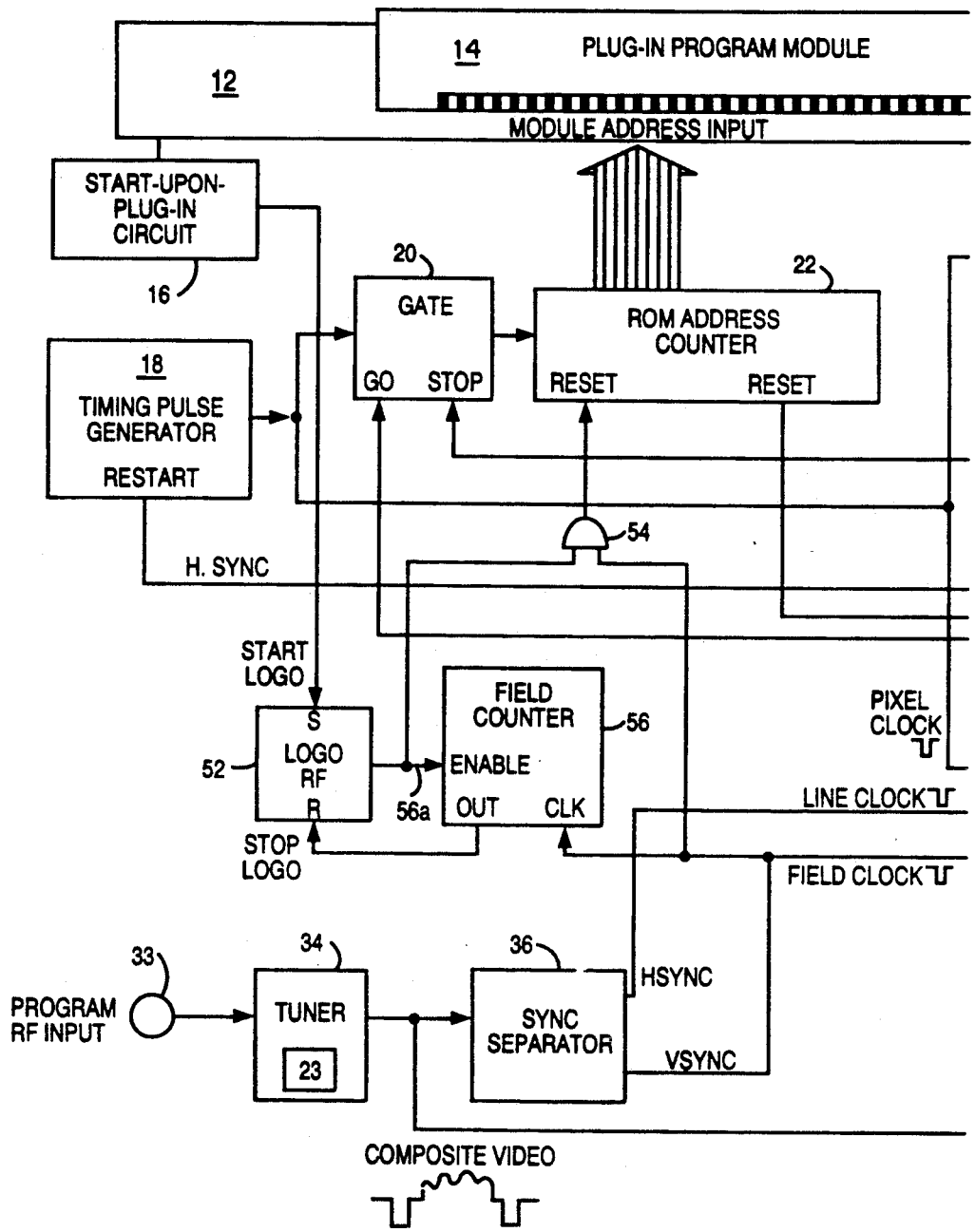
Figures 2, 6:
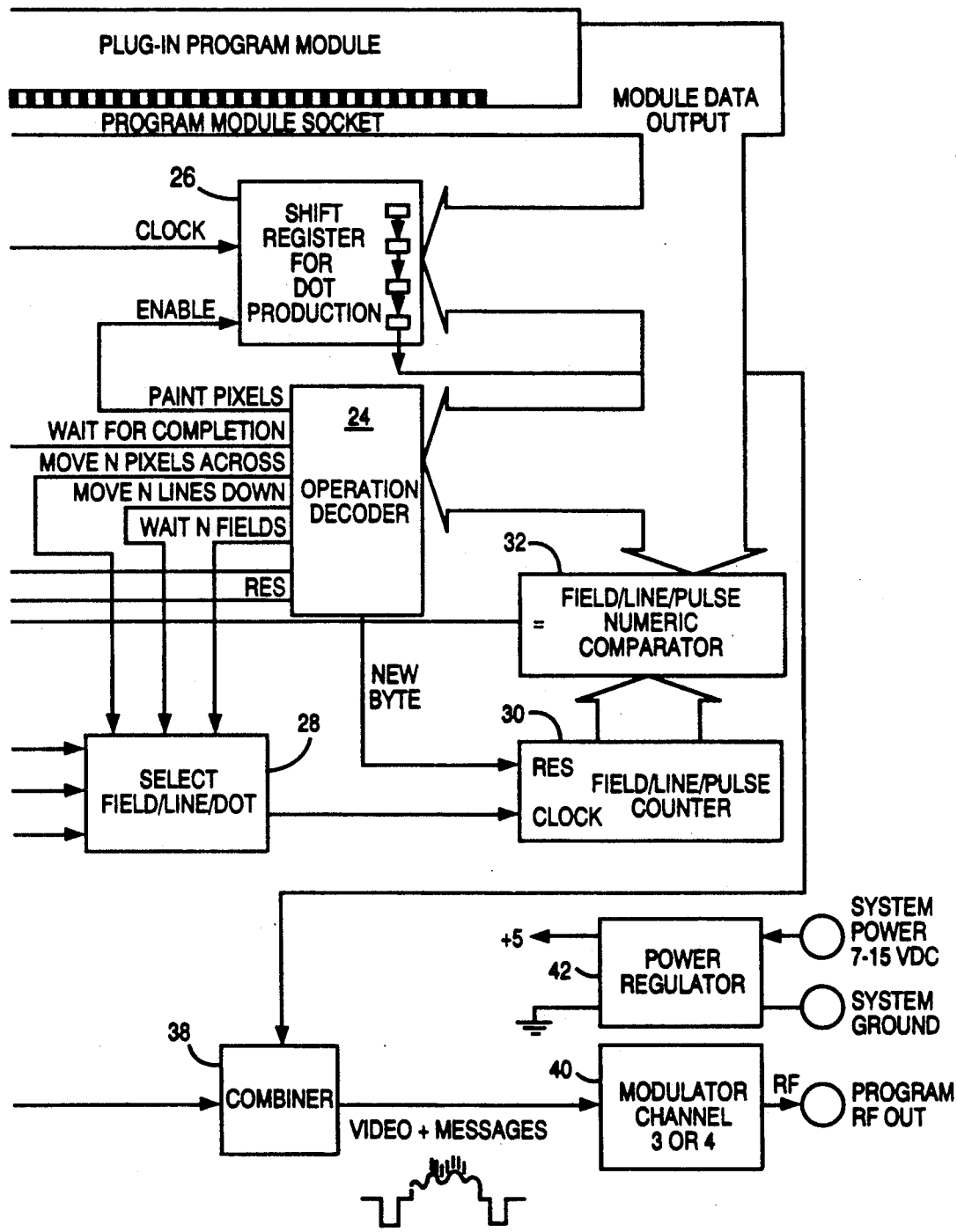
Figures 2, 8:
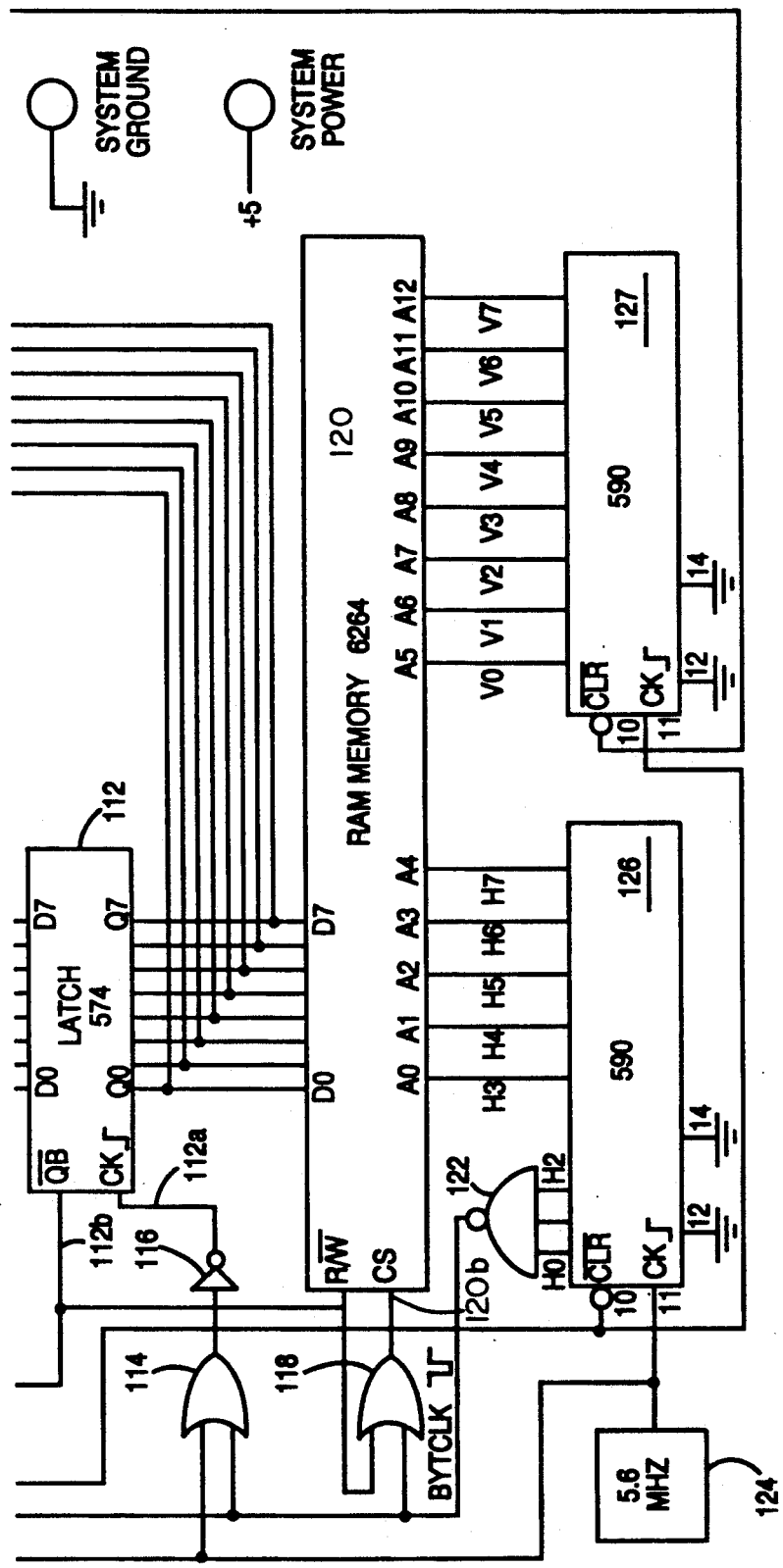

The above, as well as other objects of the present invention will become apparent when reading the accompanying description and drawings in which:

FIGS. 1-1 and 1-2 taken together, shows a block diagram of a system for creating a display message and which is designed in accordance with the principles of the present invention;

FIGS. 2-1 and 2-2 taken together, comprise is a detailed, schematic diagram of the system shown in FIG. 1;

FIG. shows a block diagram of another alternative embodiment of the present invention for generating an audio message;

FIGS. 4-1 and 4-2, 5-1 and 5-2, 6-1 and 6-2 and 7-1 and 7-2, respectively taken together, are block diagrams of alternative embodiments of the present invention for providing additional functions and capabilities beyond those obtained through the embodiment of FIG. 1;

FIGS. 8-1 and 8-2, taken together, show is a block diagram of an embodiment for mixing video signals which have substantially the same signal formats; and FIGS. 9a and 9b-1 and 9b-2 together, show the embodiment of FIG. 6 in greater detail.

DETAILED DESCRIPTION OF THE INVENTION AND THE PREFERRED EMBODIMENTS THEREOF

FIG. 1 shows a block diagram of a message generating apparatus 10 embodying the principles of the present invention and comprising a program module socket 12 for receiving a plug-in program module 14 which may, for example, be comprised of a READ ONLY MEMORY (ROM) having a substantial storage capacity. For example, the memory may be an 8K memory capable of storing 8K bytes (actually 8196 bytes), each byte being an 8 bit binary word. The ROM 14 is preferably a plug-in module provided with electrical connectors (not shown for purposes of simplicity) capable of interconnecting with the program module socket 12a which in turn, electrically couples the ROM to the system. A sensing circuit 16 develops an output at 16a which resets the system 10 upon insertion of module (ROM) 14 into socket 12.

Timing pulse generator 18, responsive to a horizontal (line) sync signal at its restart input 18a generates timing pulses at its output 18b. Timing pulse generator 18 is automatically restarted upon the occurrence of each line sync signal applied to its restart input 18a in order to insure accurate synchronization between the composite video signals and the message signals, in the manner to be more fully described in connection with FIG. 9a, for example, to accurately locate the image data relative to the left-hand edge of the video image, for example. In the preferred embodiment, the frequency rate of generator 18 is 5.6 MHz.

Timing pulses at output 18b of generator 18 are coupled to input 20a of gate 20 which receives an enabling signal at its GO input 20b and a disabling signal at its STOP input 20c. When an enabling signal is applied to input 20b, at least one timing pulse from generator 18 is passed through gate 20 to the clock input of ROM address counter 22 which generates an address applied to ROM 14 through the program module socket 12a to read out the contents of the data in the selected memory address presented to socket 12 by counter 22. Counter 22 is reset by a reset signal derived from operation decoder 24 which sequentially receives each instruction code retrieved from the ROM 14 provided in socket 12 to initiate various operations including timing pulse generator 18, gate 20, counter 22, sync signal selection circuit 28, and counter 30. The restart instruction code is further employed to initiate a new operating cycle, as will be more fully described.

Comparator 32 compares the data word retrieved from ROM 14 with the count developed in counter 30 to open gate 20.

Data retrieved from ROM 14 is transferred t latch L1.

Shift register 26 receives a group of binary bits redtrieved from memory 12 for producing a pattern of dot signals under the control of timing pulse generator 18 and operation decoder 24. The dot signals are sequentially transferred to combiner 38 where they are superimposed upon the composite video signal and in precise synchronism therewith.

The RF input 33 receives the modulated carrier signal and applies the signal to tuner 34, demodulating the modulated carrier to derive the composite video signal which is simultaneously applied to sync separator 36 and one input of combiner circuit 38. Sync separator circuit 36 extracts the frame (field) sync signals and the line (i.e., horizontal) sync signals, which signals, together with the timing pulse signals developed by generator 18, are applied to the sync select signal circuit 28.

The remaining input 38b of combiner 38 receives the data representing the desired dot pattern. The output of combiner 38 is applied to modulator circuit 40 for modulating an RF carrier with the composite video signal combined with the message signal. The output of modulator 40 may be coupled to a conventional television receiver TV for display purposes.

The system power input 42a may derive power from a wall adapter (not shown) which converts a 60 Hz, 120 v signal to a dc value in the range from 7–15 vdc. Power regulator 42 smoothes the dc input to provide regulated 5 vdc.

The operation of the system 10 shown in FIG. 1 is as follows:

The desired ROM 14 is inserted into the program module socket. Recongnition of this condition causes circuit 16 to initialize the system by clearing latch L1 (see FIG. 2) and counter 30.

The counter 22 extracts the byte stored in the first address in memory (ROM) 14. Operation decoder 24 examines at least two of the binary bits, decoding these two binary bits to activate one of the outputs of operation decoder 24 according to the binary states of the bits examined by decoder 24. The two examined bits are typically referred to as the instruction code portion of the byte retrieved from ROM 14.

The bits examined from the byte extracted from ROM 14 are the two right-hand-most bits of the byted (see FIG. 2-2), which is preferably an 8 bit byte.

The address counter 22 thus selects the byte in the first memory address. The instruction code of the retrieved byte is applied to decoder 24 and the count portion of the retrieved byte is applied to comparator 32 (by latch L1). Decoder 24 decodes the instruction bits of the byte which, in the present example, is a "Move N Lines Down" signal, also identified as a "wait N lines" signal which is represented by the binary code "01". The six remaining binary bits represent the number of lines (i.e. line sync pulses) to be counted before performing the next step in the operation. These six binary bits from memory are applied to comparator 32. The "wait N lines" signal generated by decoder 24 enables selection circuit 28 to pass horizontal (i.e., line) sync pulses at the output of sync separator 36 through sync selection circuit 28 to the clock input of counter 30. The gate 20 prevents any further clock pulses from reaching address counter 22.

When the count in counter 30 compares with the six bit count applied to comparator 32 from ROM 14 (i.e., through latch L1), comparator 32 applies an "equal" signal to GO input 20b of gate 20 enabling a pulse from timing pulse generator 18 to be passed through gate 20 to advance address counter 22 by one count.

The byte located at the next address in ROM 14 is extracted from memory 14 and is retained in latch L1. The instruction code bits of the byte in latch L1 are applied to decoder 24 and the remaining bits are applied to one set of inputs of comparator 32. The decoder output "Wait For Completion" blocks gate 20 from transferring timing pulses to the address counter 22 until the two counts applied to comparator 32 are equal.

The instruction bits now represent the binary code "10" which are decoded to enable the "Move N Bit Positions Across" decoder output line, enabling selection circuit 28 to pass timing pulses from generator 18 through selection circuit 28 to the clock input of counter 30.

Timing pulse generator 18 has a frequency rate of 5.6 MHz for generating pulses at a rate to obtain precisely 256 dot positions per horizontal line. Each horizontal sync signal applied to restart input 18a restarts the timing pulse generator 18 to be assured that the timing pulses generated are always in precise synchronism with each horizontal sync pulse, i.e. with the left-hand edge of a video image, to assure proper timing of the 256 dot positions along each line so that the dots of like dot positions on adjacent lines are in vertical alignment.

When the number of timing pulses accumulated by counter 30 compares with the binary code applied to the other input of comparator 32 from ROM 14 (through latch L1), gate 20 is again opened to pass a timing pulse and increase the count of address counter 22, causing the next address in memory to be selected. The binary bits of the instruction code forming part of the byte extracted from memory are "11" indicating a "Paint Dots" instruction, the "Paint Dots" output of decoder 24 is enabled and the gate 20 prevents the transfer of pulses from generator 18 pending completion of the transfer of the dot pattern to combiner 38. The four left-handmost bits of the byte extracted from memory are tranferred into shift register 26 (see FIG. 2). The "Paint Dots" (or Paint Pixels) output of decoder 24 enables shift register 26. Timing pulses from pulse generator 18 applied to the clock input 26a of shift register 26 cause the four bits in shift register 26 to be shifted toward the output of register 26 in serial fashion. Binary 1 bits are applied to one input 38b of combiner 38 and are additively combined with the composite video signal in combiner 38 whereas binary 0 bits applied to combiner input 38b have no effect upon the portion of the composite video signal applied to input 38a of combiner 38. The binary 1 signals create dots which add to the brightness of the picture causing the message to appear to "float" in front of whatever picture information appears at each position along a line receiving a dot. As an alternative, the message may be presented against a dark or black background when the image of the composite video signal is omitted.

The two binary bits from the byte last extracted from memory and positioned to the right of the two instruction bits and the left of the four dot pattern bits are coupled to one input of comparator 32. The timing pulses from generator 18 are applied to counter 30 and when the four bits in shift register 26 are shifted out of the register, the counter 30 will reach the count of decimal 4 causing comparator 32 to enable gate 20 to pass a timing pulse to counter 22 in order to select the next byte from memory.

Bytes representing dot patterns are successively extracted from memory 14 to paint (i.e. generate) dots. When the number of dots to be "painted" on the horizontal line have been completed, the program counter is advanced by one count to select the next byte which contains a "wait-for-N-lines" (i,.e., move N lines down) instruction code "01" with a binary count of 1 causing the next line to be selected for painting a dot pattern. Of course, in the event that the next line is not to be selected, the count will obviously be greater than the count of 1.

Once the next line is reached, the next byte is extracted from memory by incrementing the program counter by one count under the control of comparator 32. The "Skip Dot Positions" instruction code "10" controls the number of dot positions to be skipped from the beginning of the present line before the "painting" of dots is initiated. When the appropriate skip dot positions count is reached, comparator 32 advances program counter 22 by one count to select the next byte in memory 14 which concludes the "Paint Dots" instruction code. The requisite number of "Paint Dots" instruction codes are sequentially extracted from memory and the dots to be generated at each position are combined with the composite video signal in the same manner as was previously described until the next horizontal line is completed, at which time the next byte is extracted from memory, the next byte being a wait-for-line signal which is typically accompanied by a binary count of one to advance to the next horizontal line.

When all of the dots of the message have been completed, the next byte is extracted from memory. The instruction code of the next byte is examined by decoder 24. When the two most significant binary bits are "00", the decoder decodes this information as a "Wait N Fields" command. The remaining 6 bits of the 8 bit byte are applied to one set of inputs of comparator 32 while the "Wait N Fields" output of decoder 24 is activated to cause selection circuit 28 to couple the frame sync pulse input line of sync separator 36 to the clock input of counter 30. The "wait for completion" output of decoder 24 closes gate 20 to halt the transfer of timing pulses to address counter 22 until the "Wait N Fields" operation is completed. The occurrence of each vertical (i.e. "frame") sync pulse advances counter 30 by one count.

The output of counter 30, which is also preferably a 6 bit counter, is applied to a second set of inputs of comparator 32. When the count of counter 30 compares with the 6 bit binary code applied to comparator 32 from the byte stored in the selected address of ROM 14, comparator 32 applies an enabling signal to the GO input 20b of gate 20 applying a timing pulse from generator 18 to counter 22, advancing the count in counter 22 by one count, and clearing the latch L1 (see also FIG. 2) in readiness to receive the next byte selected from ROM 14.

The instruction code of the next byte is the code "111" which comprises a reset code for resetting address counter 22. The advantage of employing a reset code of binary "111" resides in the fact that the unprogrammed address positions in ROM 14 are initially placed in the binary 1 state in the unused memory areas assuring that the ROM will always automatically reset even in the event that address counter 22 is erroneously advanced to an unused address in memory due to a spike or glitch occurring in the system, thereby assuring automatic resetting of counter 22 whenever an unused memory address is accessed.

The reset condition automatically initiates a new cycle which is performed in the same manner as was described hereinabove. The repetition rate of the subliminal message is determined by the frame sync pulse count contained in the "Wait N Fields" byte.

The standard broadcast television signal is an interlaced signal. Since the invention just described operates on only one of the two interlaced fields, the message to be displayed is present for only 1/60th of a second instead of 1/30th of a second which latter time is the time interval required for creating two interlaced fields. The system of the present invention works equally well when it is desired to generate a data image in two adjacent, interlaced frames, as will be more fully described in connection with FIG. 7.

The resolution of the system of the present invention (256 dot positions by 225 lines) is sufficient to create alphabetic and numeric characters as well as symbols and even graphic patterns for a static (non-moving) as well as a dynamic (moving) display.

If desired, the bytes representing the positions to be painted may comprise dot information wherein each dot may have a brightness which varies within a predetermined range. For example, an 8-bit binary word representing a dot to be painted may include the "Paint Dots" instruction code "11", the next three bits may represent a count from 0 through 7 which may represent an analog value of the brightness of a dot; and the next three bits may represent a second digital count from 0 through 7 representing the analog value of the brightness of the next dot. The binary information may be applied to digital-to-analog converter 44 wherein each three bit binary word is converted to an analog signal, which analog signal is applied to resistor R and is then combined with the composite video signal through combiner 38, thus providing a dot signal whose amplitude may vary within the range of analog signals converted from the three-bit binary codes for each dot. The "Paint Dots" instruction code may be employed to apply a count to the comparator sufficient to convert the two digital counts to analog values and to transfer these analog values to the combiner 38.

FIGS. 2-1 and 2-2 show a detailed schematic of the system 10 shown in FIGS. 2-1 and 2-2 in block diagram form (like elements being designated by like numerals). The socket 12 is shown as having its address terminals A0 through A21 respectively coupled with the outputs of address counter 22 comprised of three Type 74HC590 counter circuits manufactured, for example, by Texas Instruments.

Timing pulse generator 18 is comprised of operational amplifier OA, resistor R1 and capacitor C2. The start-upon-plug-in circuit 16 is comprised of a bridging member 16a, resistor R2 and gate G1 for initializing the system by clearing address counter 22, latch circuit L1, which receives the 8 bit byte extracted from memory.

Comparator 32 is a Type 74HC688 circuit manufactured, for example, by Signetics Corporation and which compares the count in counter 30, which is a Type 590 counter similar to address counter 22, with the count transferred to latch circuit L1, which may be a Type 74HC273 latch manufactured by Texas Instruments, for generating a compare signal for application to gate G3 and inverter I1.

Decoder circuit 24 is a Type 74HC139 manufactured, for example, by Signetics Corporation and is adapted to receive the Instruction code data from two bit positions of latch L1 for generating one of the four outputs dependent upon the state of the two bit binary code inputted to decoder 24.

Shift register 26 is a Type 74HC166 manufactured, for example, by Signetics Corporation and adapted to receive four bits from each eight bit byte loaded into latch L1 and for sequentially shifting out each dot signal from its output 26a to combiner 38, comprised of a resistor R3 coupled to conductor C2.

Gate 20 is comprised of AND gates G9, G10 and G11, OR gate G12 and inverters I1 and I2. The output of tuner 34 shown in FIG. 1—1 is coupled to sync separator 36 comprised of transistors Q1 through Q3, resistors R4 through R13 and capacitors C3 through C7, for delivering the horizontal and vertical sync signals respectively to gates G8 and G6, gates G4 through G8 comprising the select field/line/dot sync signal circuit 28 shown in FIG. 1-2.

The operation of the detailed circuit arrangement shown in FIGS. 2-1 and 2-2 is substantially similar to the system shown in FIGS. 1-1 and 1-2 and will not be described in detail herein, for purposes of simplicity.

The differences in FIG. 2 are as follows:

The dot pattern bits transferred into shift register 26 in parallel are shifted out of register 26 controlled by logic circuits. Since the number of bits in each dot pattern portion of a byte is always four (4), the first two outputs, H0 and H1, of the first stage of address counter 22 are utilized for counting. The H0 and H1 outputs are coupled to the clock input 26c of register 26 by gates G14 and G15, eliminating the need for providing a count as part of the dot pattern byte. The dot pattern bits are thus shifted out of the register 26 and applied to combiner resistor R3 in serial fashion.

When a count of four (4) is reached, the logical circuitry including gates G13 and G9 cause gate 20 to pass a timing pulse to advance address counter 22 when a dot pattern instruction code is present, as decoded by decoder 24, gate G9 being enabled during the presence of a dot pattern instruction code.

In order to significantly reduce the number of dot pattern bytes required to create a large string of similar dots, the dot pattern initiating a string of dots (of either binary "0" or binary "1" state) has its last dot bit to be applied to combiner 38 coupled to the input stage. When the bit in the input stage is transferred to the output stage and appears at output 26b (after four timing pulses), the opening of gate 20 causes address counter 22 to advance by one count and thereby select the next byte in memory 14. This byte is similar to a line position byte since it contains a line position instruction code and a "count". The "count", however, represents the number of continuous dots (or absence of dots) to be printed along a line.

Since the line position instruction code does not provide an enable signal to shift register 26, due to the fact that there is no dot pattern instruction code present at this time, the desired dot condition from the previous dot pattern byte remains at the output 26b of register 26 and its binary state is continuously applied to resistor R3 of combiner 38 as each timing pulse is generated.

The timing pulses are applied to counter 30 through gates G5 and G4. When the count of timing pulses counted in counter 30 compare with the "count" forming part of the line position count byte, comparator 32 causes gate 20, through inverter I1, to advance the address counter 22 to select the next byte from memory 14.

The six bit "count" permits the system to generate a string of sixty-seven (67) continuous binary bits of the same state (i.e. "0" or "1") through the use of only two bytes, namely the dot pattern (4) of the byte containing the bit state to be repeated and the line position count (63) of the byte following the desired dot pattern byte. In the absence of this unique data compression technique it would be necessary to provide seventeen (17) bytes (each having four (4) dot bits) to represent a continuous string of data of the same dot state.

In the event that it is desired to create a continuous string of dots of the same state greater in number than sixty-seven, the line position count byte may be followed by another line position count byte. For example, assuming it is desired to generate one hundred dots of the same binary state, this may be accomplished using only three (3) bytes, namely a dot pattern byte providing four (4) dots, a first line position count byte providing sixty-three dots, and a subsequent or second line position count byte providing thirty-three dots. Creating one hundred dots of the same binary state would require twenty-five dot pattern bytes in the absence of this unique compression technique, thus significantly reducing the amount of bytes required in such situations.

As an alternative embodiment, the output of register 26 may be fed back to the input causing the contents to recirculate, thus permitting the pattern of dots (i.e. the pattern of binary states) stored in register 26 to be repeated according to the "count" contained in the line position count byte (or bytes) following a dot pattern byte. This latter technique permits pattern of any combination of dots to be repeated.

Figure 3:
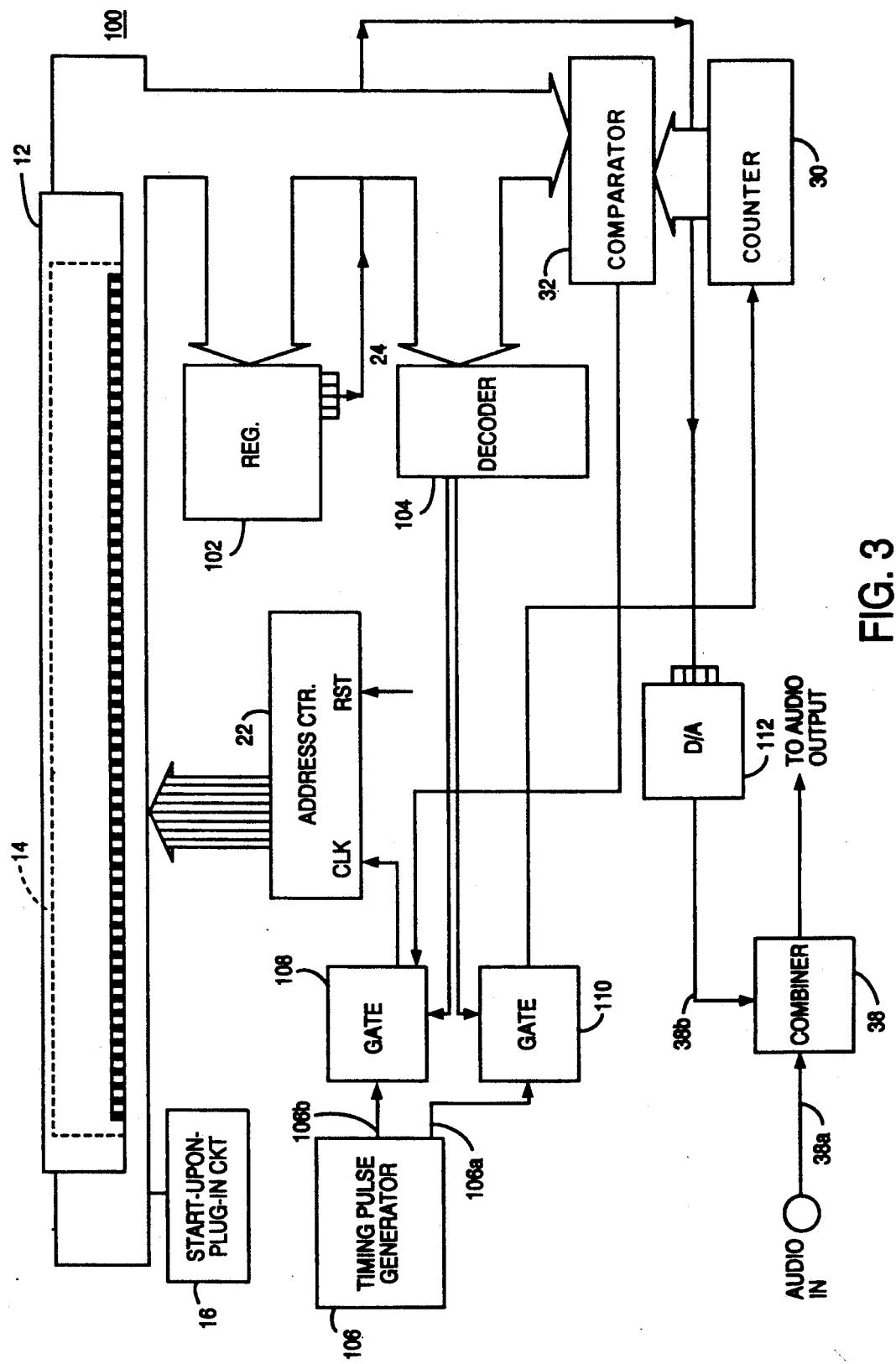

FIG. 3 shows a system 100 for generating an audio output message which may be combined with an audio signal.

The operation of the system 100 is as follows (wherein like elements as between FIGS. 1 and 3 are designated by like numerals):

When ROM 14 is inserted into module socket 12, the system is energized by circuit 16 causing the system to be reset. At this time, address counter 22 extracts the byte in the first memory address which selects the timing or refresh rate of the message, i.e., the rate at which the message to be generated is repeated. The instruction code for the wait-for-message instruction is applied to decoder 104 causing the timing pulse generator 106 to apply pulses from its low frequency pulse output 106a through gate 110 to counter 30. When the count compares with the count applied to the other set of inputs of comparator 32 by the byte extracted from memory, comparator 32 enables gate 108 to pass a timing pulse from the high frequency timing pulse output 106b of timing pulse generator 106 through gate 108 to address counter 22 to advance the address counter 22 by one count, causing the selection of the byte stored in the next memory address. The byte may represent one "slice" of audio information employing five binary bits of the 8-bit byte, for example, which may represent any one of 32 possible values over a voltage range of from 0 to +5 volts, for example. The five-bit binary word is applied to register 102, is converted by digital-to-analog converter 112 and is applied to input 38b of combiner 38 to be combined with the audio signal. Each successive byte is read out of ROM 14, converted into analog form and then combined with the audio signal by way of combiner 38. The two right-hand-most bits identify the nature of the byte, i.e., that the 5 binary bits represent a portion of the message (audio) signal.

In the event that a pause is to be provided between successive message elements, a pause or wait for next audio signal (i.e., wait-for-next word) instruction may be provided to cause decoder 104 to activate gate 110 to provide a predetermined delay between the last sound element (or "slice") and the next successive sound element to be generated, with the delay being determined by the binary count of the last byte extracted from memory which binary code is compared with the count of low frequency pulses applied from the low frequency pulse output of generator 106 through gate 110.

When the sound elements to be generated have been completed, a reset instruction code is then extracted from memory to initiate a new cycle.

If desired, the audio signal may be synchronized from the frame and, in fact, with the line signals of the video composite signal simply by providing a composite video signal and applying the frame and line sync signals to the counter 30. If desired, both audio and video messages may be combined with the audio and video signals of the television receiver, by mixing the RF and the audio sub-carrier, to obtain the audio sub-carrier, demodulating the sub-carrier to obtain the audio signal, combining the digitally stored audio message with the audio signal accompanying the composite video signal, and modulating the sub-carrier with the combined signals for decoding by the television receiver. The frame sync signals may be counted for or used for timing.

Figures 1, 4:
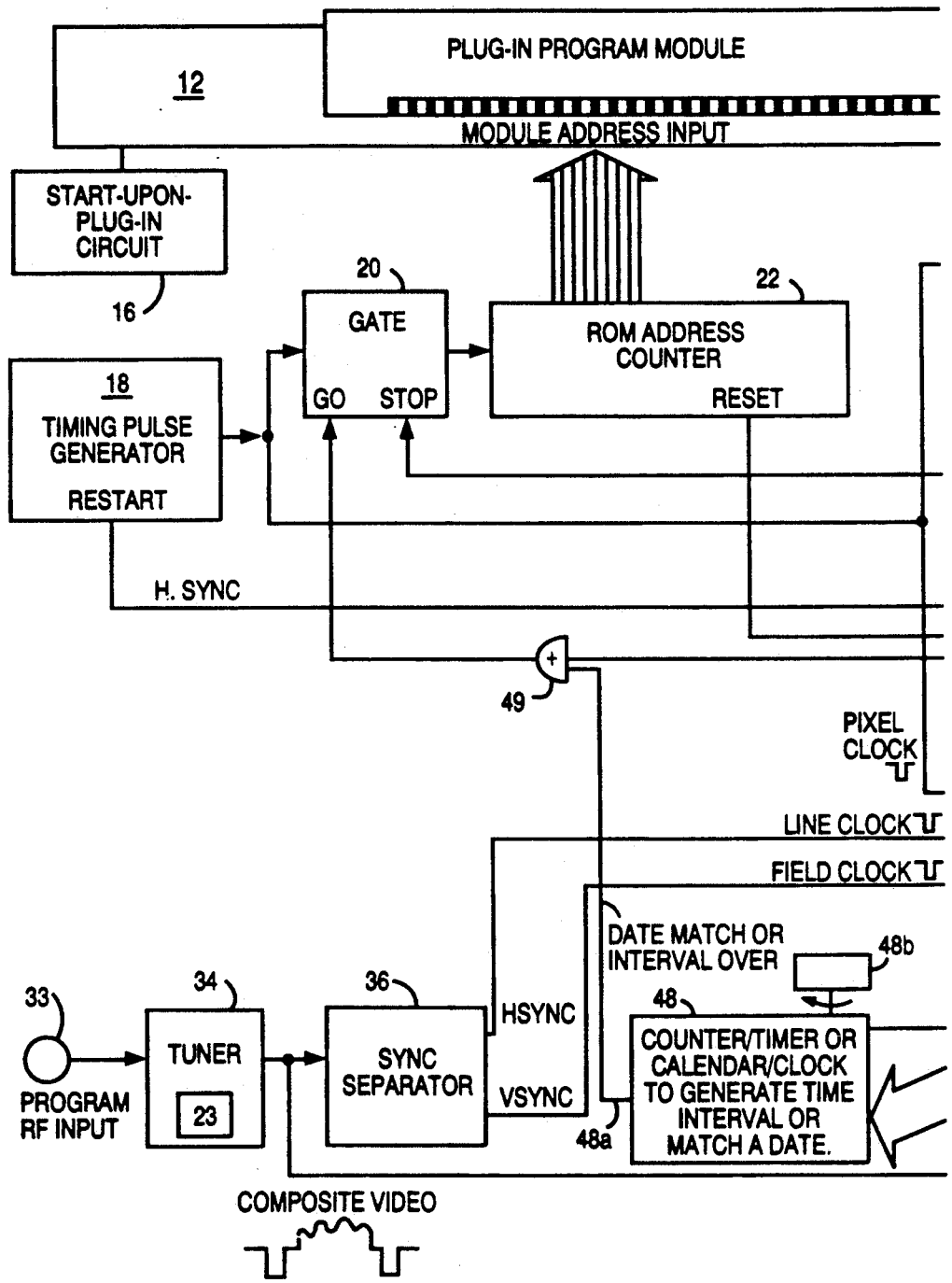
Figures 2, 4:
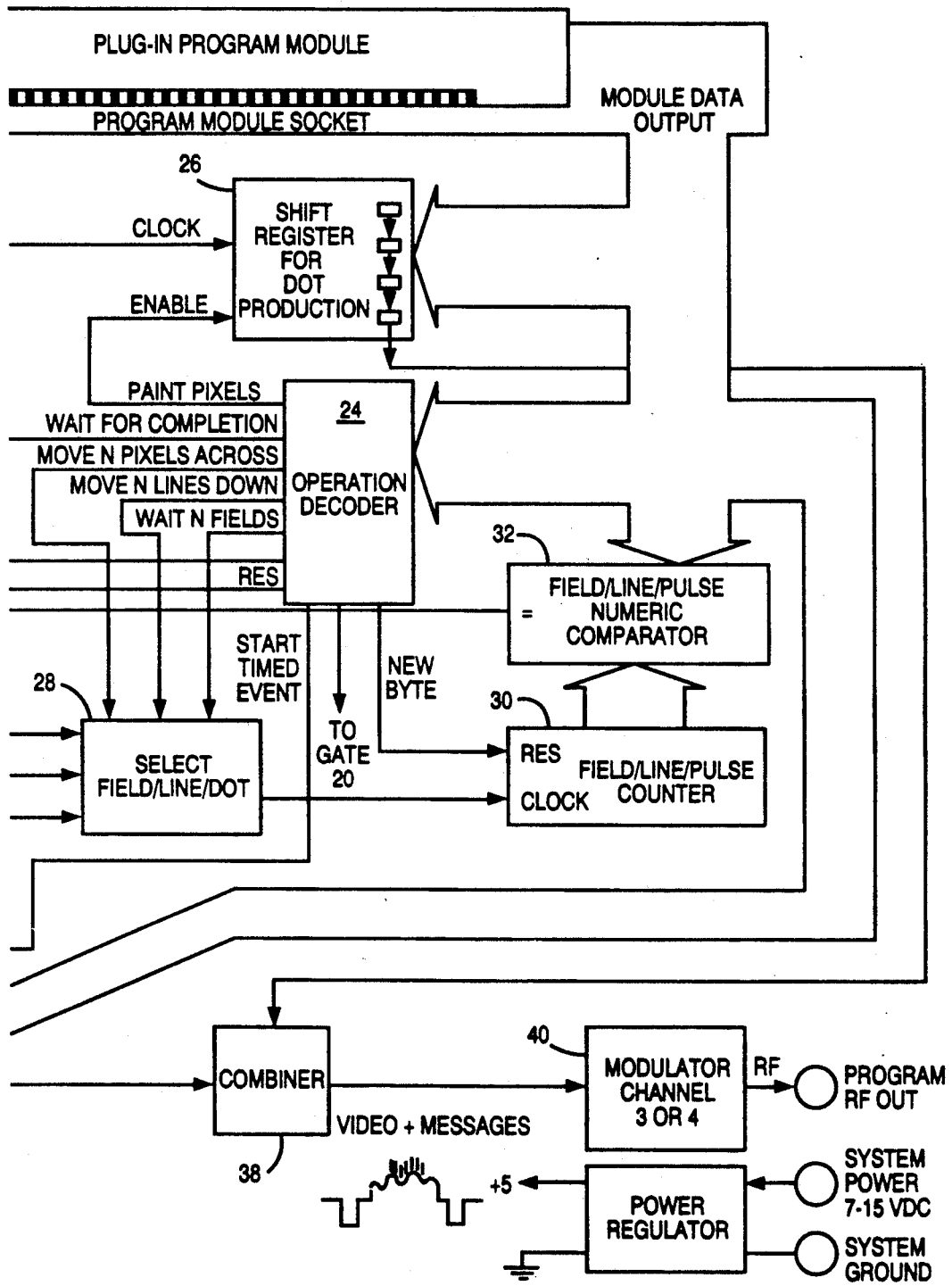

FIGS. 4-1 and 4-2 show an arrangement in which a timer is provided to display messages at predetermined intervals. For example, the embodiment of FIGS. 4-1 and 4-2 may be employed to generate reminder messages at various times during the day such as: remindng a young viewer to run an errand; reminding an older viewer to take some medicine; reminding a viewer of an appointment; etc.

A byte including an instruction code identifying a timed event and a count is stored in memory 14.

When the byte is extracted from memory, decoder 24 decodes the Start Timed Event instruction code and triggers the calendar/clock to load the count portion of the Start Timed Event byte which is transferred to clock 48. Since the data required to properly identify the time of the event (for example, year, month, day, time of day) may require two or more bytes, the decoder also advances the address counter to retrieve the required bytes in a sequential manner. The last byte halts the incrementing of address counter 22 by providing an instruction code which prevents opening of gate 20. The above functions may be accomplished by providing two types of Start Timed Event instruction codes, namely a code which loads the event portion of a byte into the calendar/clock and advances the address counter to retrieve the next byte in memory and a code to load the event data portion of the last byte of a group of bytes representing the time of event data into the calendar clock and then start the calendar/clock 48.

Calendar/clock 48 compares the internally generated time data with the data transferred from memory. At this time all other operations are halted, i.e. no further bytes are extracted from memory. When the internally generated time compares with the time of event information retrieved from the Start Time Event bytes, clock 48 generates an increment pulse, which is passed by OR gate 49 to open gate 20. The next byte selected from memory 14 is the first byte of the message to be displayed upon the television screen. This first byte and subsequent bytes are sequentially retrieved from memory 14 and their data bits are added to the composite video signal through combiner 38 in the same manner as the system of FIGS. 1-1 and 1-2 described hereinabove. The display may either be subliminal or may persist for a given time interval, for example, by employing the method and apparatus shown in FIGS. 7-1 and 7-2, as will be described hereinbelow.

As an another alternative, the clock/calendar 48 may be set by the user operating the setting control 48b and, upon reaching the set time, generate a start signal at 48a which causes the address counter to step to the first address storing the "reminder" message.

Figures 1, 5:
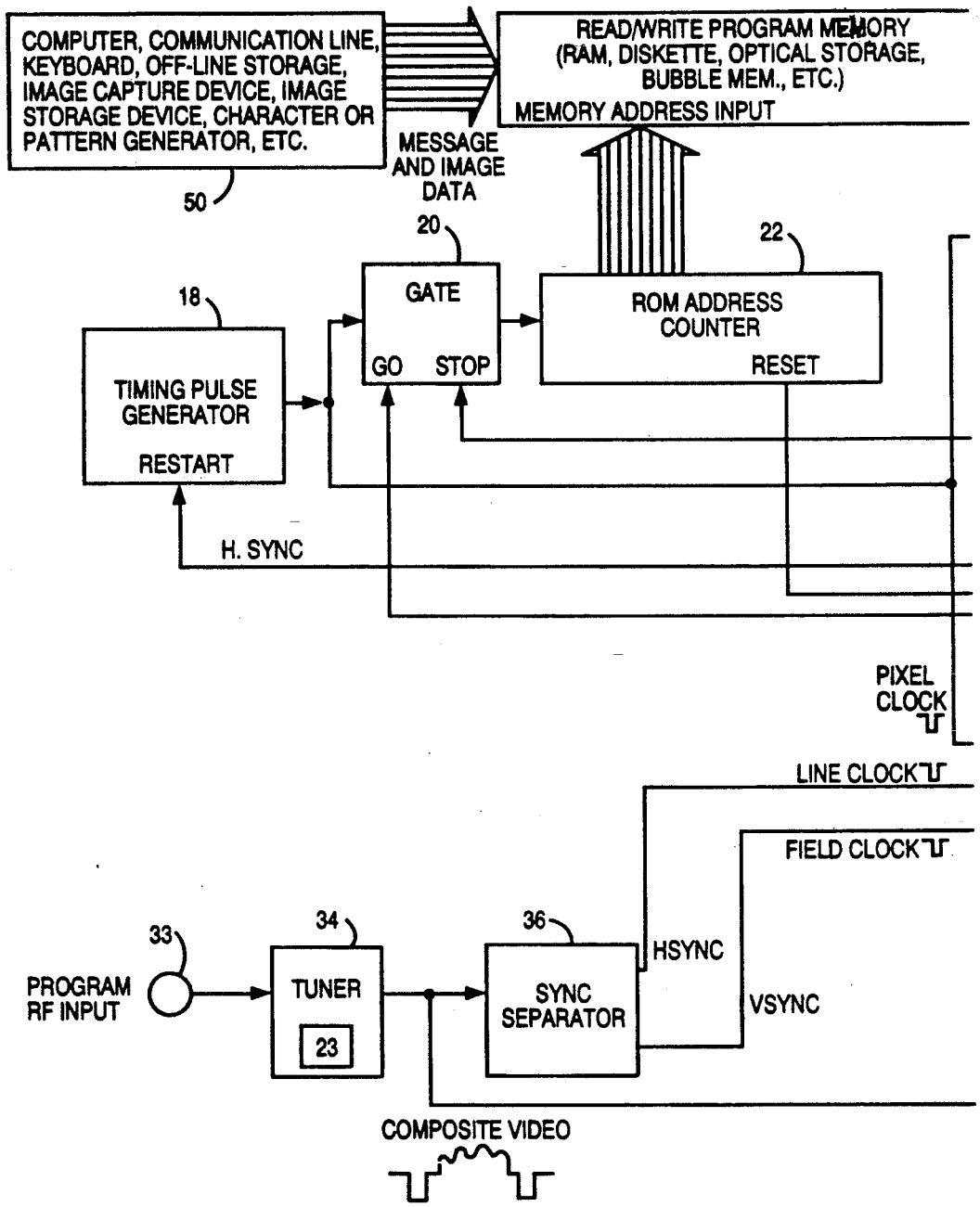
Figures 2, 5:
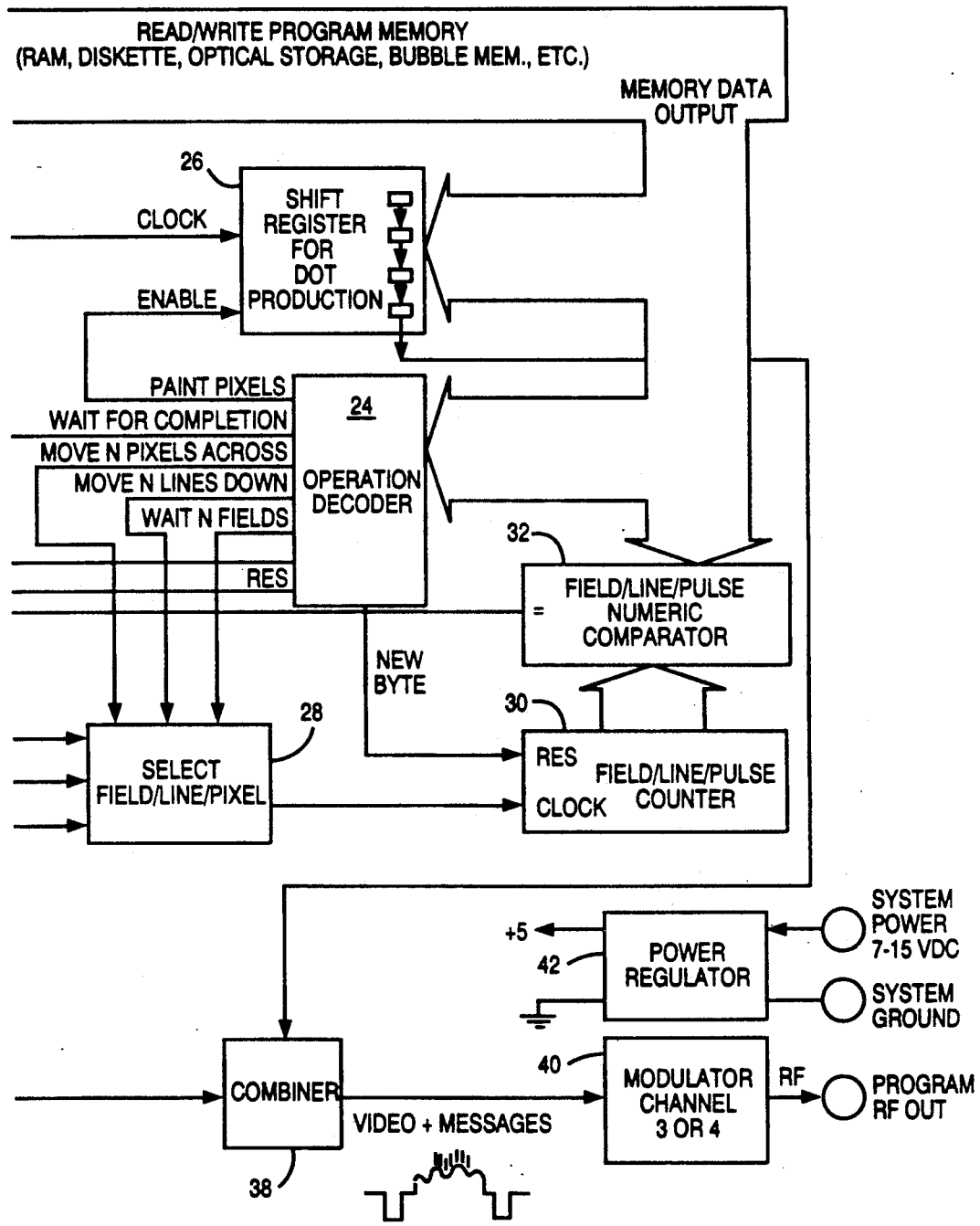

FIGS. 5-1 and 5-2 shows another alternative arrangement of the present invention in which the data to be combined with the composite video signal may be derived from a variety of sources.

For example, as was previously described, memory 14 may be a RAM, a ROM, a magnetic diskette, a bubble memory or other like storage device capable of high speed data retrieval.

The data stored in memory 14 may be derived from a variety of sources such as a computer, a communication line, a wireless transmission, off-line storage means, an image capture device, an image storage device, a character or pattern generator or other like source of data, represented as data source 50 in FIGS. 5-1 and 5-2. The data from source 50 is transferred to memory 14 either in an off-line technique or in a real-time technique, depending on the operating capability of the data source.

For example, a message may be created at a computer keyboard and transferred to memory 14 as the data is being created or as a block of data transferred from the computer memory (not shown) after the desired message has been created, thus permitting a subliminal (or steady) message to be created using a variety of data sources. The data transferred to memory 14 is retrieved from memory 14 in the manner described in connection with FIGS. 1-1 and 1-2 and will not be repeated here for purposes of simplicity, it being noted that the arrangement of FIG. 5 is substantially the same as that shown in FIG. 1.

FIGS. 6-1 and 6-2 show an arrangement which may be employed to introduce an introductory image into the composite video signal. In cases where it is desired to introduce the subliminal program material through a persistent initial image, the start circuit 16 sets a bistable flip-flop 52 which applies an enable signal to gate 54 and to the enable input 56a of a field counter 56. Each frame sync pulse from sync separator 36 resets address counter 22 so long as an enable signal is present at the output of flip-flop 52. Thus, the introductory message is repeated during each successive frame. Field counter 56 counts the number of successive frame sync pulses. The field counter 56, upon reaching a predetermined count, develops a stop enable signal at its output 56c to reset flip-flop 52 and prevent resetting of address register 22 to thereby halt the refreshing of the introductory message. Field counter 56 is provided with a count capability sufficient to enable the introductory message to persist for a period which may lie in a range from one (1) to ten (10) seconds, for example, before termination. the introductory message may consist of the company name and/or logo, the program title, instructions or introductory remarks, for example. As an example, the field counter may be provided with a count capacity of 240 to cause the introductory image to persist for four (4) seconds (each frame being 1/60th of a second in duration).

Figure 7:
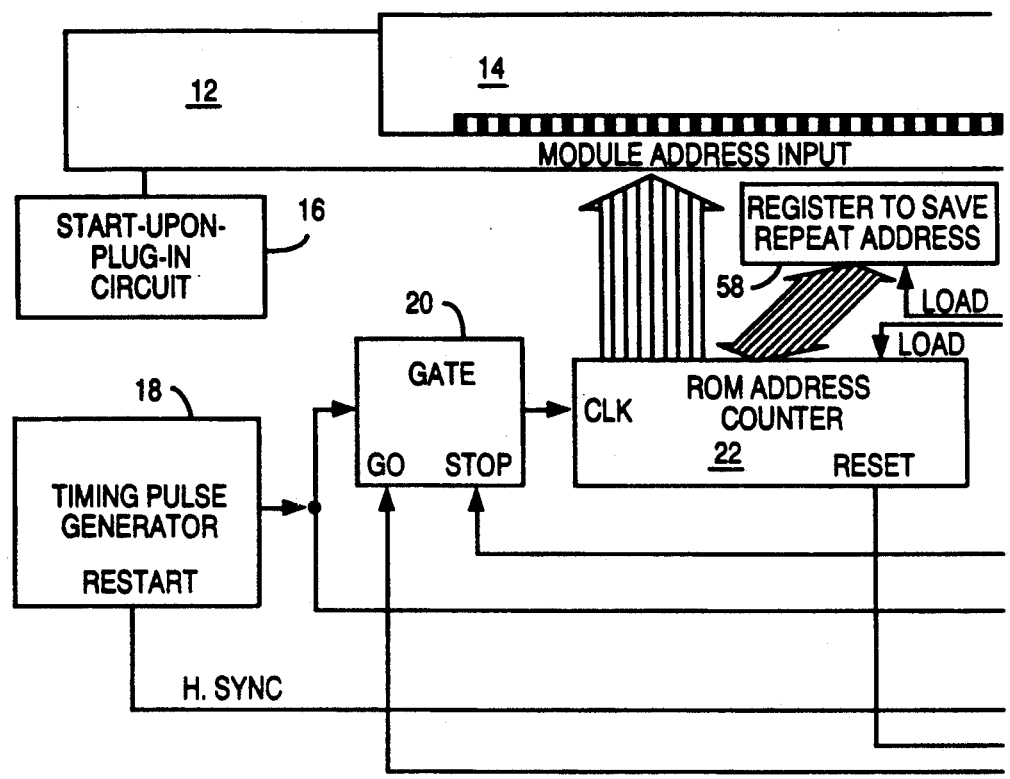
Figure 1:
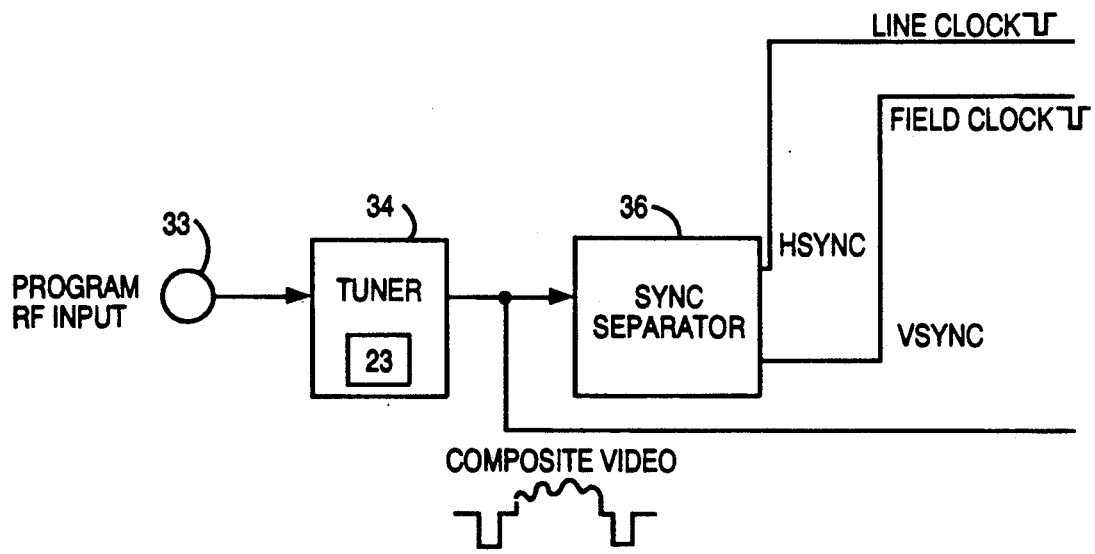
Figures 2, 7:
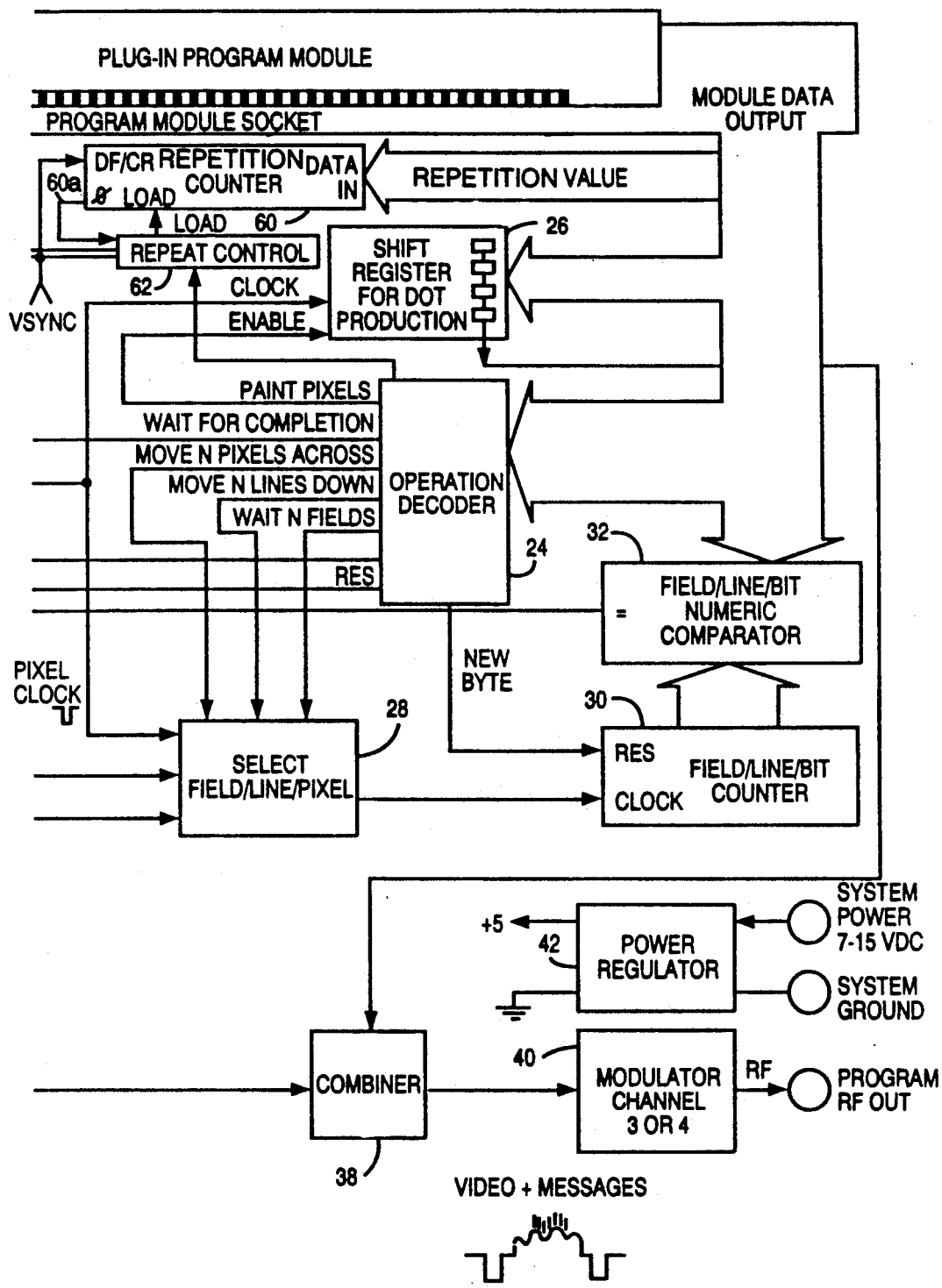

FIGS. 7-1 and 7-2 shows another modified arrangement in which a segment of a program stored in memory 14 may be repeated as often as is desired without storing the bytes comprising the program segment in memory at a multiple number of locations. The modified system shown in FIGS. 7-1 and 7-2 is similar to that shown in FIGS. 1-1 and 1-2 with the addition of a register 58 for storing a repeat address, a repetition counter 60 and a control logic circuit 62.

When a repetition value is transferred into counter 60 and a repeat control code is transferred to decoder 24, the repeat control circuit 62 is activated by decoder 24 causing the next address in address counter 22 to be transferred to register 58 and saved. The saved address is retained in register 58 until needed.

Counter 60 is loaded with the count forming part of the repeat byte and decremented by one count by the occurrence of each frame sync pulse. When counter 60 has counted down to zero, output 60a enables repeat control circuit 62 which transfers the address stored in register 58 to program counter 22 to cause the group of bytes comprising the program segment to be repeated by returning to the address of the first byte of the message segment to be repeated.

As one example, the segment may be repeated when it is desired to generate the message during the occurrence of both of the interlaced fields of a single frame. Thus, the subliminal image may be repeated through the method and apparatus shown in FIGS. 7-1 and 7-2, wherein the message is repeated twice, i.e. once during each of the interlaced fields making up one frame.

As another alternative, the segment may be repeated to provide a persistent image (i.e. not a subliminal image) which remains on the display screen for several seconds or more. This is accomplished by repeating the desired message portion at a repetition rate which is sufficient to create a continuous message in the mind of the observer. For example, for a four (4) second message the count may be 240 counts (i.e. 240 frame sync pulses occurring at both second intervals).

Figure 9A:
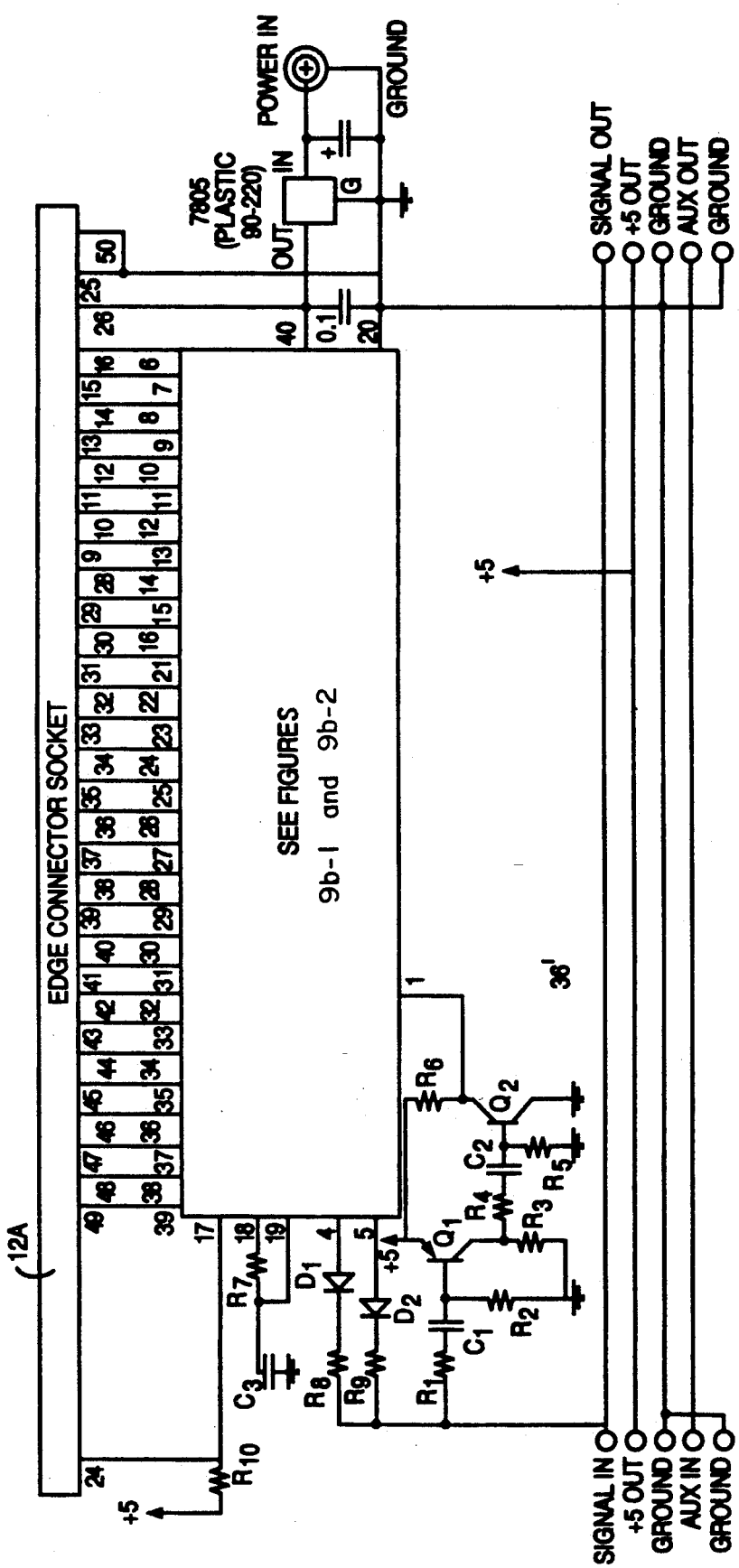
Figures 1, 9B:
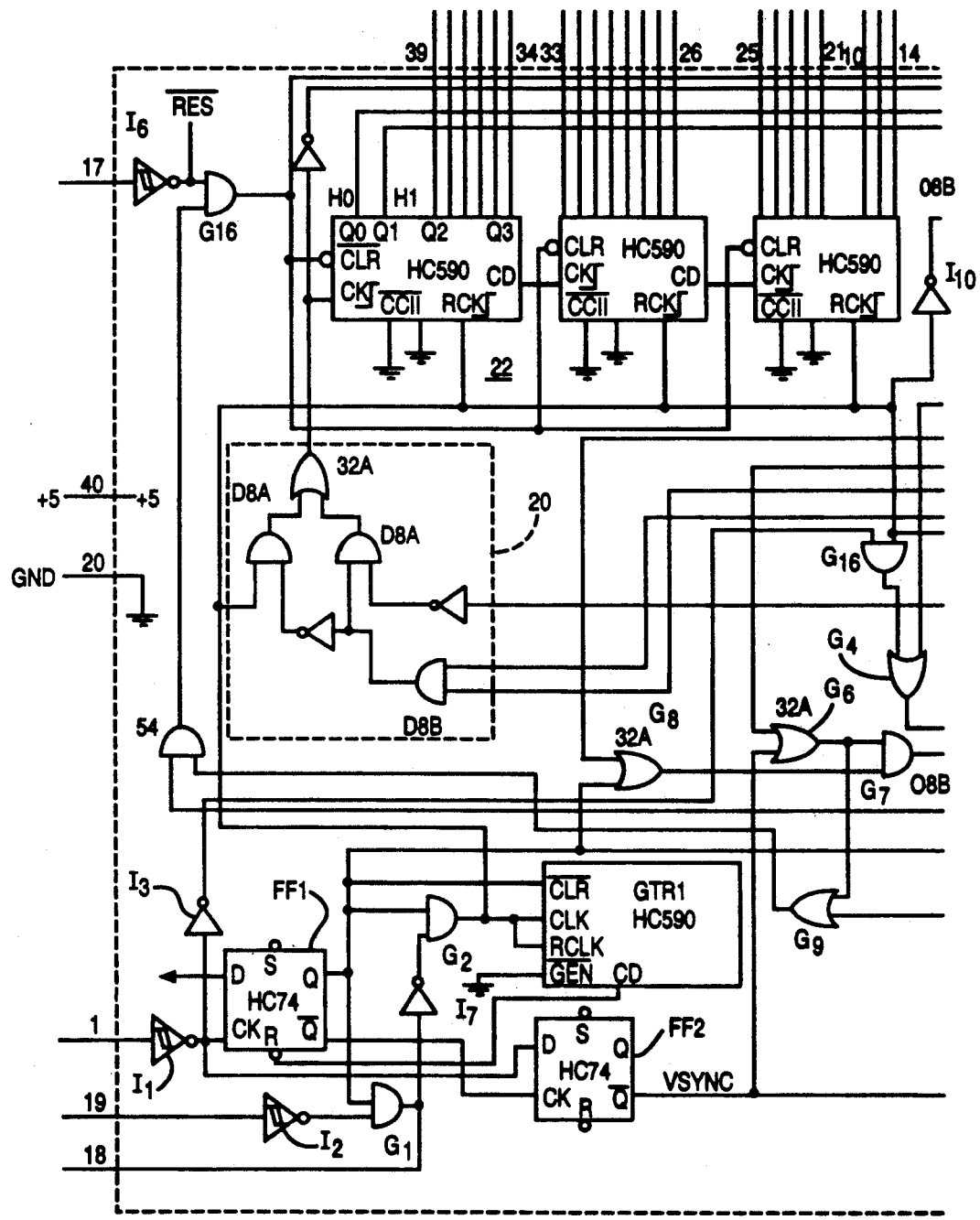
Figures 2, 9B:
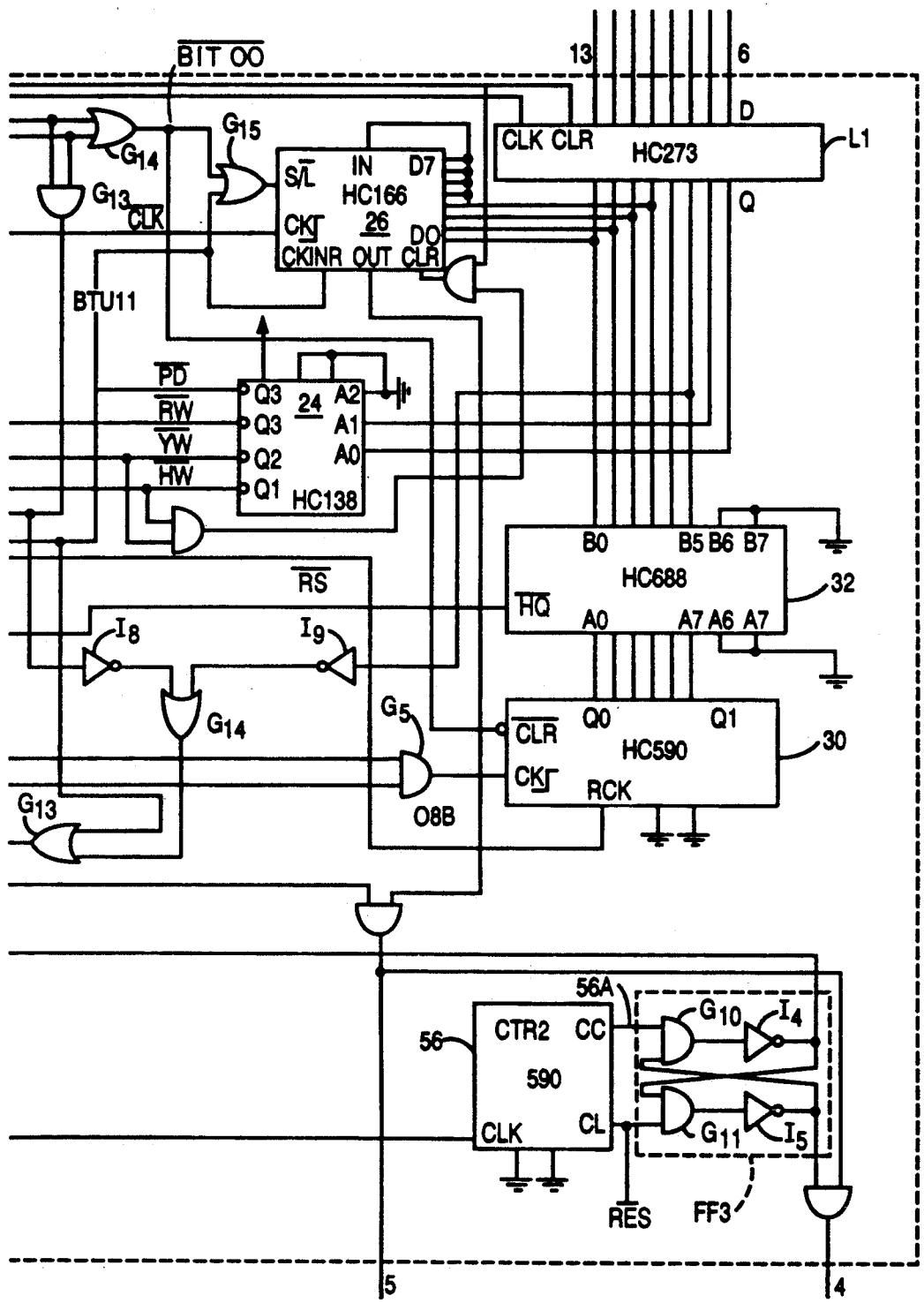

FIGS. 9a, 9b-1 and 9b-2 taken together show the embodiment of FIG. 6 in greater detail, FIG. 9a showing the electrical interfacing between the circuitry of FIGS. 9b-1 and 9b-2 and the incoming composite video signal and the television receiver/display.

A description of the operation of the embodiment of FIGS. 9a, 9b-1 and 9b-2 is as follows:

Considering FIG. 6-1 and 6-2, the program RF input which is applied to input 33 is demodulated by tuner 34 to remove the carrier. The composite video signal is then applied to the Signal-In terminal of FIG. 9a. The circuit 36' comprised of the resistors R1 to R6, capacitors C1 and C2 and transistors Q1 and Q2 extracts the synchronizing signals (line and frame sync) and applies them to connector terminal 1 of the circuit shown in FIGS. 9b-1 and 9b-2. The synchronizing signals are applied to the clock input of a flip-flop circuit FF1 through inverter I1. Upon the occurrence of the first negative leading edge of a sync pulse, this condition is inverted by inverter I1 causing the Q output of FF1 to be set high. This high level directly provides a clear input to counter CTR1, provides an enable pulse to gate G1, restarting the timing pulse generator comprises of inverter I2, resistor R7 and capacitor C3, respectively coupled to the circuit of FIGS. 9b-1 and 9b-2 through connectors 18 and 19, respectively. The timing pulse generator is thus restarted and pulses are applied through gate G2 to the clock input of counter CTR1 when the Q output of FF1 is high.

The Q output of FF1 is also coupled to one input of gate G3 to enable the dot signals at the output of shift register 24 to be combined with the composite video signals coupled to the Signal-In/Signal-Out line shown in FIG. 9a through connector 5.

The composite video signal appearing at the output of inverter I1 is coupled to one input of gate G16 through inverter I3 for selectively providing horizontal sync signals to counter 30 for use in the compare operations in which comparator 32 compares the count developed in counter 30 with the count in latch L1 in the same manner as was previously described. The remaining input of gate G16 is coupled to the output of gate G2 to selectively apply timing pulses to counter 30 through gates G16, G4 and G5. The gates G16, G4, G5, G6 and G7 collectively form the select circuit 28 shown in block diagram form in FIG. 1-2, for example.

Counter CTR1 accumulates timing pulses until it reaches its counting capacity (255), whereupon its output CTR1a provides a reset pulse for resetting FF1 whose Q output goes low and whose $\bar{Q}$ output goes high thereby: turning off the timing pulse generator by way of gate G1; blocking timing pulses from reaching counter CTR1 by way of gate G2; blocking timing pulses from reaching gate G3; and applying a positive going level to the clock input of flip-flop FF2 whose D input is coupled to the output of inverter I1. The timing pulse generator is thus turned off briefly and is restarted by the occurrence of the next horizontal sync pulse.

The count capacity of counter CTR1 is chosen so that its output CRT1a goes high just prior to initiation of the next horizontal sync pulse and during the latter portion of a vertical sync pulse, the time duration of a vertical sync pulse being substantially equal to the duration of six lines of a single field video image (comprised of 225 lines). FF2 has its $\bar{Q}$ output go low when the level at its D input is high, which it normally should be, causing the $\bar{Q}$ output to develop a vertical or frame sync pulse which is applied to the clock input of counter CTR2 and to one input of gate G6 for selectively coupling vertical sync pulses to counter 30 through gates G7 and G5. Counter CTR2 coincides with the field counter 56 shown in FIG. 6-1 and counts vertical sync pulses. Gates G10 and G11 and inverters I4 and I5 collectively comprise a flip-flop circuit FF3 which coincides with the bistable flip-flop circuit 52 shown in FIG. 6-1. One output of FF3 is coupled to the input of a gate G15 whose other input is coupled to the output of gate G3 for coupling the dot signals to the Signal Out line through connector 4, diode D1 and resistor R8.

As was described hereinabove in connection with FIGS. 1-1 and 1-2, insertion of a plug-in memory into connector socket 12a couples an electrical ground condition through connector 24 (see FIG. 9a) to drop the level at resistor R10 to zero. This voltage level is coupled through connector 17 to inverter I6 to develop a reset pulse $\overline{RES}$, which reset pulse is simultaneously applied to one input of gate G16, the clear input of counter 56 and one input of FF3 to enable gate G15 to cause dot pulses to be applied to the Signal-Out line through gates G3 and G15 and connector 4 and simultaneously to apply a clear condition to the clear inputs of the three counter circuits making up the address counter 22 by way of gates G9, 54 and G16. The address counter 22 is thus cleared upon the occurrence of the first vertical sync pulse and then comes under the control of the timing pulses selectively applied through gate 20 to selectively generate addresses for each byte in memory which comprise the introductory or "logo" image.

Flip-flop circuit 52, together with gates G6, G9, 54 and G16, assure that each subsequent vertical sync or frame pulse developed at the $\overline{Q}$ output of FF2, will cause the program counter to be reset upon completion of read-out of all the bytes which collectively generate the "logo" image frame. The OR gate G6 and the OR gate G9 both function substantially as negative-AND gates. Gate G6 changes from low to high when Q of FF2 goes high and the field wait (FW) line of decoder 24 is low. Gate G9 goes from low to high when the output of gate G6 goes from low to high and the output from FF3 is low. Gate 54 goes high when G9 goes high. A timing pulse from gate G2 determines the duration of the output pulse developed by gate 54. Gate 16 goes high when $\overline{RES}$ is high and the output of gate 54 is high. $\overline{RES}$ is high as long as a memory 14 is plugged into its memory socket.

The counting capacity of counter 56 is selected dependent upon the length of time it is desired that the "logo" image persists upon the television screen. Assuming a four second display time, counter 56 is provided with eight binary stages, thus providing a capability of developing a count of 256 or slightly more than four seconds. When the counting capacity of counter 56 is reached, output 56a resets flip-flop 52 preventing vertical sync pulses from being applied to the clear inputs of the address counter 22 and also causing subsequent dot signals developed by the system to be passed directly through gate G3 and coupled to the signal output line through connector 5, diode D2 and resistor R9.

Thus, after the "logo" image has persisted for approximately four seconds, program counter 22 no longer repeats the retrieval of the "logo" image and is now permitted to generate address codes beyond those which identify the bytes which comprise the "logo" image and thereafter extracts bytes from memory 14 which represent the subliminal image or any other image to be displayed by the television display.

When the address counter 22 retrives the restart code, which occurs after all of the data stored in memory has been retrieved, although address counter 22 returns to the first address in memory and will thus retrieve all the bytes which comprise the "logo" display, the "logo" display will persist for only one frame during the second and subsequent addressing and retrieval of all of the bytes in memory 14.

The byte retrieval, line counting, frame counting and dot combining operations performed by the circuitry of FIGS. 9a, 9b-1 and 9b-2 are substantially the same as those described in connection with FIGS. 1-1 and 1-2, for example.

FIGS. 8-1 and 8-2 show another embodiment of the present invention in which the data to be superimposed with a composite video signal is derived, for example, from a storage means such as a video tape recorder (VTR). The system 80 converts the message information into digital form and then sequentially combines each digital signal with program data in synchronism with the program sync signals.

The system 80 comprises a message video input 82 derived, for example, from the output of a video tape recorder (VTR) (not shown). Comparator 84 extracts the message sync pulses (frame and line sync pulses) from the message input signal and applies the message sync pulses to gate 90.

Comparator 86 extracts the message video signals, converting them to levels of either binary "zero" or binary "one", depending upon whether the instantaneous value of the message signal is above or below a predetermined threshold, and applies its output to the clock input of bistable flip-flop FF1 (98) and the input 108a of serial-to-parallel converter 108 comprised of a shift register which shifts each data level into the register as a discrete data bit under control of a timing pulse. Each data bit is shifted through the stages of register 108 at a rate established by clock 124, which develops pulses at a rate of 5.6 MHz.

The message video output of comparator 86 is normally devoid of message data and the system 80 is thus normally in a quiescent state. As soon as message information is received, the first such positive going pulse developed by comparator 86 sets the Q output of FF1 (98) high.

The first frame sync pulse from sync separator 94 sets the Q output of FF2 (100) high under control of the high output at Q of FF1 (98) which is applied to the D input of FF2 (100). This places the system 80 in the "store" mode, which provides a write level signal at the read/write (R/W) input of RAM memory 120 and a load condition at the input 112b of latch 112.

Address counter 126, comprised of an eight bit counter stage develops a "byte count" of 8 at its outputs H0, H1 and H2. At a byte count of eight, gate 122 provides an output causing the eight bit byte developed in register stage 108 to be latched into latch 112, and transferred into RAM 120, by means of a byte clock pulse generated at the output of gate 122 and coupled to the clock input 112a of latch 112 by gate 114 and inverter 116 and which pulse is also coupled to input 120b by gate 118. The byte in latch 112 transferred to memory (RAM) 120 is stored in a memory address determined by the address code of the horizontal outputs H3–H7 of address counter 126 and the vertical outputs V0–V7 of address counter 127.

The register 108 continues to receive message video signals from comparator 86. The binary state loaded into the input stage of register 108 is determined at the leading edge of each clock pulse applied to the clock input 108b by clock 124. Each group of eight binary pulses sequentially transferred into register 108 are then latched into latch 112 and loaded into RAM 120 in parallel fashion.

Each such byte is transferred to an address in RAM 120 determined by outputs H3–H7 of address counter 126 and V0–V7 of address counter 127. As each eight bit data byte is generated, the count of address counter 126, as developed by outputs H3–H7, is advanced by one count. Each horizontal (line) sync pulse from gate 92 (derived from the message sync signals) clears address counter 126 and advances counter 127 by one count.

The program (i.e. line and frame) sync pulses are extracted from the program video signal, applied at input 81, by means of comparator 94, which applies the program sync pulses to gate 88. During the store mode of the operation the Q output (a high condition) of FF2 (100) permits the message sync pulses from comparator 84 to be passed by gate 90 to gate 92, while the $\overline{Q}$ output of FF2 (a low condition) prevents the program sync pulses from being passed by gate 88. Thus, synchronization of the message data is established by the message line sync signals during the store mode.

The sync separator 94, during the store mode, extracts a message vertical (frame) sync pulse from the output of gate 92 and simultaneously applies the frame sync pulse as a clock pulse input to bistable flip-flops 100 (F2), 102 (F3), and 104 (F4) as well as the clear input 127a of address counter 127, which receives horizontal (line) sync pulses from gate 92 to clear address counter 126 and simultaneously advance the count in address counter 127 upon the occurrence of each line sync pulse. FF4 (104) resets FF2 (100) causing the system to enter the read-out mode. The Q output of FF2 (low level) blocks the message sync pulses from being applied to gate 92 by gate 90 while the $\overline{Q}$ output of FF2 (high level) permits the program sync signals to be passed by gate 88 to gate 92 causing synchronization during the read-out mode to be controlled by the program sync pulses.

Each byte read into RAM 120 is extracted from memory during the read-out mode. A read (high) level from the Q output of FF2 is applied to the read/write (R/W) input 120b of RAM 120. Each byte is transferred from RAM 120 to parallel-to-serial converter 109 which is comprised of a shift register. The eight bit byte transferred in parallel to converter 109 is then transferred out of register 109 in serial fashion at a rate determined by pulses from clock 124 and applied to clock input 109b. The binary signals are sequentially applied to analog switch 96 causing switch 96 to apply a medium "gray" condition to the program video signal upon the occurrence of each dot condition (i.e. the binary state representing the presence of a dot). The count of counter 126 is cleared and the count of counter 127 is advanced one count by each horizontal (i.e. "line") sync pulse from the program sync pulses. The derived count developed by counter 126 is advanced by pulses from clock 124.

Flip-flop 104 resets flip-flop 100 each time a frame (i.e. "vertical") sync pulse is applied to its clock input 100b, so that every other frame sync pulse initiates a store mode and the intermediate frame sync pulses initiate a read-out phase.

The analog switch 96 is switched only during the presence of a dot signal to establish a medium gray level at the occurrence of each dot. The timing of the message information is based upon and synchronized with the program sync signals establishing precise synchronism between the message and program data.

If desired, the gray level may be either a flat color overlay for color display systems or may be a constant medium gray level or some other level to suit the needs of the particular application.

The combined signal appearing at terminal 97 may be used to modulate a carrier preparatory to application to a television display similar to that shown in FIGS. 1-1 and 1-2, for example.

As another alternative, the analog switch 96 may be replaced by the combiner 38 of FIG. 1-2 whereby the program (composite video) signal is present during the entire operation when the message information is combined with the program information.

The gates 106 and 110 prevent parallel-to-serial converter 109 from putting out a signal whenever a frame or line sync pulse is present.

A latitude of modification, change and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

For example, the timing pulse generator 18 of FIG. 1—1 may be replaced by a timing pulse generator having an output whose freqwuency is $2^N$ times greater than the desired output frequency. A divider circuit coupled to the output of the timing pulse generator divides the output frequency by $2^N$ to obtain the desired frequency, where $N=1, 2, 3, \ldots$ The stages of the divider circuit, which are preferably bistable flip-flop circuits, are reset by each line sync pulse while the timing pulse generator is continuously free-running. For example, the timing pulse generator may be operated at four times the desired operating frequency [$(2^2) \times 5.6$ MHz] and the divider circuit may be comprised of two bistable flip-flop stages to divide the output frequency by four, i.e. [22.4 MHz $\div (2^2)$]. As another example, the timing pulse generator may have an output frequency of eight times 5.6 MHz and be provided with a three stage divider for dividing the output by eight to obtain an output frequency of 5.6 MHz. This technique reduces the phase error of the timing pulses while maintaining the timing pulse generator in a free-running state.

The overlay signals stored in memory 14 shown in FIG. 1—1, may be combined with a composite signal from which the image information may be removed either prior to or at the time that the signals are being combined, thus providing a composite signal which produces the overlay message against a black background in place of the background image created by the composite video signal. The image portion of the composite video signal may be omitted only during the frame in which the overlay message is developed. For example, the frame and/or line sync pulses may be utilized to replace the image information forming part of the composite video information by a constant signal level chosen to provide a dark or black background. The line and frame sync pulses of the composite video signal are retained for synchronizing purposes in order to create the video display.

What is claimed is:

1. A method for combining information comprising a string of data signals with a video signal in a synchronous manner according to the frame and line sync signals forming part of said video signal together with the information signals, comprising the steps of:
   (a) providing a frame count, a line count, a horizontal position count and a plurality of data;
   (b) generating timing pulses at a predetermined frequency;
   (c) counting line sync signals;
   (d) counting said pulse signals when a predetemrined line sync signal count is reached;
   (e) sequentially combining each data signal of said information with said video signal;
   (f) counting frame sync signals; and
   (g) repeating steps (b) through (e) when a predetermined frame sync signal count is reached.

2. The method of claim 1 further comprising the steps of successively combining the data signals with the composite video signal responsive to the occurrence of the last line sync pulse; and combining the data signals with the composite video signal responsive to the next line sync signal when the data signals associated with the last line of the composite video signal has been combined with the composite video signal.

3. The method of claim 1 wherein said frame and line counts and said data comprise multi-bit bytes each stored in a predetermined location in a substantially large capacity memory; and wherein step (c) further includes comparing the line sync count with the line count stored in said memory and advancing to step (d) when the counts compare;

step (d) further includes comparing the pulse signal count with the line count stored in said memory and advancing to step (e) when said counts compare; and step (e) further includes selecting the data byte from said memory for sequentially combining the data and video signals.

4. The method of claim 3 wherein each byte is comprised of an instruction portion and an information portion.

5. A method for combining information comprising a string of data signals with a video signal in a synchronous manner according to the frame and line sync signals forming part of said video signal together with the information signals, comprising the steps of:

(a) providing a line count, a horizontal position count and a plurality of data;

(b) generating timing pulses at a predetermined frequency;

(c) counting line sync signals;

(d) counting said pulse signals; and (e) sequentially combining each data signal of said information with said video signal;

said frame and line counts and said data comprising multi-bit bytes each stored in a predetermined location in a substantially large capacity memory, each byte being comprised of an instruction portion and an information portion; and said method further comprises:

step (c) further comprises comparing the line sync count with the line count stored in said memory and advancing to step (d) when the counts compare;

step (d) further includes comparing the pulse signal count with the line count stored in said memory and advancing to step (e) when said counts compare; and step (e) further includes selecting the data byte from said memory for sequentially combining the data and video signals;

a frame count being incorporated in a frame count byte comprised of a frame count instruction code and a plurality of binary bits representing the desired frame count; whereby the number of frame sync pulses are counted when a frame count instruction code is examined; and the byte in the next memory address is extracted when the number of frame sync pulses counted compares with the frame count.

6. The method of claim 5 wherein the byte extracted from memory is the line count byte comprised of a line count instruction code and information for selecting one of the lines of the video image and further comprising the step of counting line sync pulses responsive to the line count instruction code and extracting the next byte in memory when the count of line sync pulses compares with said line count.

7. The method of claim 6 wherein the last-mentioned byte extracted from memory is a line position count byte comprised of a line count instruction code and data representing a line position count; and further comprises the step of counting said timing pulses responsive to the line position count instruction code and extracting the next byte in memory when the count of timing pulses compares with the line position count.

8. The method of claim 7 wherein the last-mentioned byte extracted from memory is a generate dot byte comprised of a generate dot instruction code, a count and a group of binary bit signals representing a dot pattern to be generated and further comprising the step of counting said timing pulses responsive to a dot generation instruction code; and successively combining each binary bit signal with the composite video signal and extracting the next byte from memory when the number of timing pulses compares with the count included in the dot generation byte.

9. The method of claim 7 wherein the last-mentioned byte extracted from memory is a generate dot byte comprised of a generate dot instruction code and a group of binary bit signals representing a dot pattern to be generated and further comprising the step of counting said timing pules responsive to a dot generation instruction code; and successively combining each binary bit signal with the composite video signal and extracting the next byte from memory when the number of timing pulses reaches a predetermined count.

10. The method of claim 9 wherein said method step of successively combining the binary signals representing a dot pattern further comprises the steps of inserting said binary signals into a register and shifting binary signals out of the register in serial fashion responsive to each timing pulse; and combining each binary signal with the composite video signal as it is shifted out of said register.

11. The method of claim 10 wherein a line position count byte containing a line position instruction code and a count value is stored in the memory, said method further comprising the steps of :

recirculating the binary signals in said register as the binary signals are stepped out of the register;

extracting the line position count byte from the memory when the binary signals have been shifted out of the memory serial-shifting out the binary signals in the register responsive to said line position instruction code and said timing pulses;

accumulating timing pulses as the binary signals are shifted out of the register; and halting the shifting operation when the accumulated timing pulse compare with the line position count value.

12. The method of claim 9 wherein a line position count byte containing a line position instruction code and a count value is stored in the memory, said method further comprising the steps of:

repetitively combining the binary signals representing a dot pattern last extracted from the memory with said composite video signal a predetermined number of times determined by the count value of the line position count byte.

13. The method of calim 9 wherein the last-mentioned byte extracted from memory comprises a dot generation byte similar to the first-mentioned dot generation byte and followed by a predetermined plurality of additional dot generation bytes sufficient in number to create the dot pattern for the line presently being generated, wherein each such dot generation byte is extracted from memory in a sequential fashion for generation of the dot pattern group represented by each such dot generation byte.

14. The method of claim 13 wherein the line count byte in memory is extracted from memory after the last dot generation byte for the present line is extracted from memory, said line count byte comprising a line count instruction code and a count representing the next line to be selected for dot generation, and comprising the further steps of counting line sync pulses and extracting the next byte from memory when the count of line sync pulses compares with the line count of the last-mentioned line count byte.

15. A method for precisely positioning a dot pattern along a line of a video image comprised of a plurality of lines, said positioning being controlled responsive to line position selection data and dot generation data and utilizing a timing pulse generator having a restart input for restarting the timing pulse generator upon receipt of a signal to generate pulses at a predetermined repetition rate, said method comprising the steps of:
  (a) providing a composite video signal comprised of image information and line and frame sync pulses;
  (b) examining said line position selection data and simultaneously restarting said generator upon the occurrence of a line sync pulse;
  (c) counting the timing pulses produced by the timing pulse generator after being restarted;
  (d) examining the dot generation data when the count of timing pulses compares with a count represented by said line position data;
  (e) sequentially combining each dot signal of a group of signals in said dot generation data with the composite video signal.

16. The method of claim 15 further comprising the steps of:
  (a) initiating a count of the timing pulses; and
  (b) examining the next word in memory when the last-mentioned count compares with a count forming part of the dot generation word.

17. The method of claim 15 further comprising the steps of:
  (a) initiating a count of timing pulses; and
  (b) selecting the next word from memory when the initiated count reaches a predetermined value.

18. The method of claim 17 wherein the next word is a dot generation word and further comprising repeating steps (e) through (g) when the next dot generation word is examined.

19. A method for combining an audio signal with an audio message stored in digital format in a memory and comprised of binary words including a delay time before message word, mesage element words, dead time between message element words and an end/restart of message word and utilizing a timing pulse generator for generating pulses at a low frequency rate and at a high frequency rate, comprising the steps of:
  a. providing an audio.signal of analog type;
  b. successively extracting words from the memory;
  c. counting the low frequency pulses when a delay before message word is extracted;
  d. extracting the next word from memory when the count of low frequency pulses compares with a count forming part of the delay before message word;
  e. counting the timing pulses when a message word is extracted;
  f. converting the digital representation of an analog value forming part of the message word into an analog signal;
  g. combining the analog signal with the audio signal; and
  h. successively extracting each message word from memory and repeating steps (e) through (g) for each successive message word extracted from memory.

20. A method for combining an audio signal with an audio mesage stored in digital format in a memory and comprised of binary words including a delay time before message word, message element words, dead time between message element words and an end/restart of message word and utilizing a timing pulse generator for generating pulses, comprising the steps of:
  a. providing an audio signal of analog type;
  b. successively extracting words from the memory;
  c. counting the timing pulses when a delay before message word is extracted;
  d. extracting the next word from memory when the count of timing pulses compares with a count forming part of the delay before message word;
  e. counting the timing pulses when a message word is extracted;
  f. converting the digital representation of an analog value forming part of the message word into an analog signalf
  g. combining the analog signal with the audio signal; and
  h. successively extracting each message word from memory and repeating steps (e) through (g) for each successive message word extracted from memory.

21. The method of claim 19 further comprising the step of counting one of said timing pulse signal outputs responsive to extraction of a dead time word; and extracting the next word from memory when the last-mentioned pulse count compares with the count incorporated in the dead time word.

22. The method of claim 21 further comprising the step of returning to the address in memory storing the delay before message word upon termination of the last message word and repeating steps (b) through (h).

23. Apparatus for superimposing signals upon a composite video signal including at least frame and line synchronizing signals, said apparatus comprising
  vertical sync detecting means for generating an output responsive to each vertical sync signal in said video signal;
  line sync detecting means for generating an output responsive to each horizontal sync signal in said video signal;
  memory means for storing variable date comprising selectable frame counts, selectable line counts; and a selectable data pattern;
  means for generating timing pulse signals;
  means for selecting a frame count from said memory responsive to a reset signal;

means for accumulating outputs from said vertical sync generating means responsive to said reset signal;

means for selecting the line count from said memory means when the count in said accumulating means compares with said frame count;

means for counting output signals from said line sync detector means;

means for selecting a pulse count from said memory means when the count of line sync signals compare with said line count;

said selecting means including means for accumulating signals from said pulse generating means;

means for selecting a data word from the memory means when the pulse count compares with an accumulated count; and means for combining the bits of the data word with said video signal.

24. Apparatus for locating dot signals along a line of a composite video signal comprised of line and frame sync pulses and image information comprising:

means for extracting line sync signals from said composite video signal;

memory means for storing a line word, a line position word each having an instruction code portion and count portion and a plurality of data generation words each data generation word including a data portion and an instruction code portion and a count portion;

means for extracting a line word from said memory means responsive frame sync signal;

means for counting line sync signals responsive to an instruction code portion of the line word;

means for extracting said line position word from said memory means when the count of said line sync signals equals the count in the count portion of said line word;

a timing pulse generator for generating timing pulses;

means responsive to a line position instruction code portion in the line position word for counting said timing pulses;

means for extracting a data generation word from said memory means when the count in said counting means compares with a count portion of said line position word;

means responsive to said data generation instruction code portion for counting said timing pulses;

means responsive to said data generation instruction code portion in the data genreration word for sequentially combining bit signals representing a predetermined data pattern forming part of the data generation word with said composite video signal; and means for extracting the next word in memory when the count of timing pulses compares with the count portion of the data generation word.

25. Apparatus for locating dot signals along a line of a composite video signal comprised of line and frame sync pulses and image information comprising:

means for extracting line sync signals from said composite video signal;

memory means for storing a position word having an instruction code portion and a count portion and a plurality of data generation words each having an instruction code portion, a data portion and count portion;

means for extracting said line position word from said memory means responsive to an horizontal sync signal;

a timing pulse generator for generating timing pulses;

means responsive to a line position instruction code portion in the line position word for counting said timing pulses;

means for extracting a data generation word from said memory means when the count in said counting means compares with the count forming portion of said line position word;

means responsive to said data generation instruction code portion for counting said timing pulses;

means responsive to a data generation instruction code portion in the data generation word for sequentially combining bit signals representing a predetermined data pattern forming part of the data generation word portion with said composite video signal; and means for extracting the next data generation word in said memory means when the count of timing pulses reaches a predetermined count equal to the count portion of the data generation word last extracted from said memory means.

26. The apparatus of claim 25 wherein said timing pulse generator includes a restart input for restarting said timing pulse generator responsive to a horizontal sync pulse to assure that the timing pulses are in synchronism with the horizontal sync pulses to assure proper alignment of bits in like positions in the lines making up the video image.

27. The apparatus of claim 24 wherein said memory means comprises a plug-in module and having a plurality of addresses for storing said variable data, means for releaseably receiving said plug-in module for electrical connection of said memory means with the apparatus; and means responsive to insertion of said plug-in module in said receiving means for generating said reset signal.

28. The apparatus of claim 23 wherein said memory means is a read-only memory (ROM).

29. The apparatus of claim 23 wherein said ROM is comprised of a substantially large number of memory locations (addresses), each being capable of storing a multi-bit binary word.

30. The apparatus of claim 29 wherein each binary word ("byte") is comprised of an instruction code portion and a count portion, each instruction code being different from every other instruction code.

31. The apparatus of claim 30 wherein said data pattern comprises an instruction code portion, a count portion and a pattern portion, said pattern portion comprising a group of digital signals representing a predetermined pattern, said count representing the number of binary signals comprising said dot pattern.

32. The apparatus of claim 30 wherein said data pattern comprises an instruction code portion and a pattern portion, said pattern portion comprising a group of digital signals representing a predetermined pattern.

33. The apparatus of claim 31 further comprising a line position count stored in said memory means;

means for selecting the line position count from said memory means when the accumulated line signals compare with said line count; and said selecting means including means for selecting a data pattern from said memory means when the accumulated count of timing pulse signals compares with the count forming part of said line position count.

34. The apparatus of claim 33 wherein the timing pulse generating means comprises restart input means for restarting said timing pulse generating means responsive to a line sync signal.

35. The apparatus of claim 23 wherein said selecting means comprises address counter means for generating multi-bit address codes for extracting a word from the ROM memory located at the address whose address code is generated by said address counter.

36. The apparatus of claim 35 wherein said address counter means further includes a clock input for incrementing the count generated responsive to each signal applied to said clock input.

37. The apparatus of claim 36 wherein said address counter means further includes a reset input for resetting the address counter means responsive to a reset signal to initiate a new operating cycle.

38. The apparatus of claim 37 wherein said memory means comprises a plug-in memory means;
means for receiving said plug-in memory means including means for generating said reset signal when said plug-in memory means is inserted into said receiving means.

39. Apparatus for superimposing a graphic presentation upon a composite video signal comprised of line and frame sync signals and image information, comprising:
memory means having a plurality of address locations for storing a plurality of words containing the data necessary for generating the desired graphic presentation;
means for releaseably receiving said memory means for coupling the memory means to the apparatus;
address counter means responsive to a reset signal for applying signals representing an address in memory to said memory means through said receiving means and further including a clock input for advancing the count in said counter means;
timing pulse generating means;
gate means for selectively coupling timing pulses from said generating means to said clock input for altering the output of said address counter means;
decoder means for decoding the instruction code portions of a word extracted from said memory means;
means for temporarily storing the data bits forming part of a graphic presentation word;
second counter means;
means for comparing the contents of said second counter means with the count portion of a word extracted from said memory means;
means for extracting the line and frame sync signals from said composite video signal;
selection means for selecting one of said line and frame sync signals and timing pulse signals for application to said second counter means for accumulating a count of the signals applied thereto;
said address counter means being cleared responsive to insertion of said memory means into said receiving means;
said address counter means selecting a frame count word from its address location in said memory means responsive to a reset signal;
said decoder means operating said selection means to couple frame sync pulses to said second counter means;
said second counter means enabling said gate means to pass a timing pulse signal to said address counter means when the count in said compare counter means compares with the count portion of the word extracted from said memory means;
said address counter means extracting a line count word in the next address in said memory means responsive to a timing pulse signal;
said decoder means closing said gate means, resetting said compare counter means and controlling said signal selecting means to couple line sync signals to said second counter means;
said comparing means opening said gate to pass a timing pulse signal to said address counter means when the count in said address counter means compares with the count portion of said line count word extracted from said memory means;
said address counter means extracting a line position count word from the next address in said memory means responsive to a timing pulse signal;
said decoder means clearing said second counter means, closing said gate means and controlling said selecting means to couple timing pulses to said second counter means responsive to the instruction code portion of the line position word extracted from said memory means;
said comparing means opening said gate means when the count in said second counter means compares with the count in the count portion of the line position word extracted from said memory means;
said address counter means extracting the dot generation word from the next address in said memory means responsive to a timing pulse signal;
said decoder means closing said gate means clearing said second counter means and controlling said selection means to couple timing pulse signals to said second counter means;
combiner means having first and second inputs and an output;
said decoder means further including enable means to enable said temporary storing means for sequentially shifting the portion of the graphic presentation word representing the desired data pattern transferred into said temporary storing means to the first input of said combiner means responsive to said enable condition and said timing pulse signals; and
said combiner means input receiving said composite video signal to provide a combined signal at said combiner means output.

40. The apparatus of claim 39 wherein said timing pulse generator means further comprises restart input means for restarting said timing pulse generating means responsive to an horizontal sync signal applied to the reset input means to synchronize the timing pulses with the horizontal sync signal.

41. The apparatus of claim 39 wherein said composite video signal is derived from a carrier signal modulated by said composite video signal by tuner means for extracting said composite video signal from said modulated carrier signal.

42. The apparatus of claim 39 further comprising means coupled to said combiner means output for modulating a carrier frequency signal with the output of said combiner means.

43. The apparatus of claim 39 wherein said memory means is a plug-in read only memory means (ROM) having a plurality of address locations for storing the words employed for producing the message to be combined with said composite video signal.

44. The apparatus of claim 43 further comprising means for resetting said second counter means and said address counter means when said plug-in ROM is inserted into said receiving means, said resetting means also including means for generating said reset signal.

45. The apparatus of claim 39 wherein said data words contain graphic information wherein each position of the graphic information is represented by a group of digital signals repesenting an analog value;
digital-to-analog conversion means for converting each group of digital signals into analog form preparatory to transfer to said combiner means.

46. Apparatus for combining data with a composite video signal comprised of line and frame sync signals and image information comprising:
means for deriving line and frame sync signals from said composite video signal;
memory means for storing information in binary form representing the data to be combined with the composite video signal and position information for controlling the location of the data in the image field of the composite video signal;
means for generating timing pulses;
means responsive to said position information and said sync signals for selecting one of said lines;
combiner means having first and second inputs for respectively receiving said composite video signal and said data;
means responsive to said timing pulses and said position information for selecting data from said memory means;
means for transferring the data selected from said memory to said combiner means second input in sequential fashion; and
means for successively displaying said message at a repetition rate determined by said frame sync signals and reptition rate word stored as a count in said memory means.

47. The apparatus of claim 46 further comprising D/A means for converting the information stored in said memory means into analog form preparatory to being combined with said composite video signal by said combiner means.

48. The apparatus of claim 46 wherein said memory means is a plug-in memory means, receiving means for releaseably receiving said plug-in memory means for electrically coupling said memory means to the apparatus when said plug-in memory means in properly inserted into said receiving means.

49. The apparatus of claim 48 further comprisng means for generating a reset signal when said memory means is inserted into said receiving means.

50. The apparatus of claim 46 wherein said memory means has a storage capacity of a large number of multibit binary words.

51. The apparatus of claim 50 wherein each work is comprised of an equal number of bits at least equal to eight (8).

52. The apparatus of claim 51 wherein said memory means has a capacity of storing approximately 8196 memory locations, each storing a word (i.e., an 18K memory).

53. The apparatus of claim 52 wherein each of said addresses is capable of storing an 8 bit binary word.

54. The method of claim 1 wherein step (c) is initiated when the frame count provided at step (a) is reached at step (b).

55. The method of claim 54 wherein step (d) is initiated when the line count provided at step (a) is reached at step (c).

56. The method of claim 55 wherein step (e) is initiated when the position count provided at step (a) is reached at step (d).

57. The method of claim 56 wherein step (f) is initiated when the position count provided at step (a) is reached at step (e).

58. The method of claim 57 wherein the information provided at step (a) is stored in a memory storage device:
said information being selected from the memory storage device in a predetermined sequence.

59. The method of claim 4 further wherein the information portion is a count value and the instruction portion identifies the type of count and further comprising the step of counting a selected one of the frame, line and timing pulses according to the instruction portion of the word selected from the memory.

60. A method for repeating a pattern of binary signals comprised of a string of binary bits and an instruction code portion and further including a repeat data word comprising the steps of:
providing a memory containing said string of binary data arranged in a predetermined manner, and said repeat data word comprising binary data representing a predetermined count value;
generating timing pulses at a predetermined fixed rate;
transferring the string of binary data into a register having an output;
shifting the binary data through said register in a serial fashion for transfer to said output under control of the timing pulses until the last binary signal reaches said output;
extracting the repeat data word from the memory;
counting timing pulses;
extracting the next data word from memory when the timing pulse count compares with the count value of the repeat data word to maintain the last binary signal at the output of the register at least until said compare condition occurs.

61. The method of claim 60 further comprising the steps of providing at least one additional string of binary data in the memory, comprising an instruction code portion and a binary pattern, said method further comprising the steps of:
extracting the additional string of binary data from the memory;
clearing the register responsive to the instruction code portion;
transferring the binary pattern into the register;
shifting the binary pattern through the register to transfer each binary signal to the register output under control of the timing signals.

62. The apparatus of claim 23 wherein said memory means is chosen from a group of memory means including random access memory means (RAM); a magnetic card; a magnetic disc; a magnetic tape; and a bubble memory.

63. A method for combining first and second composite video signals each being comprised of frame and line sync signals and image data comprising the steps of:

(a) converting the image data signal of said first composite video signal into a string of pulses;

(b) storing in a memory said string of data pulses upon the occurrence of a frame sync pulse in said first composite video signal;

(c) reading out the data pulses from the memory upon the occurrence of the next succeeding frame sync pulse forming part of said first composite video signal; and (d) sequentially combining each stored data pulse with said second composite video signal.

64. The method of claim 63 wherein step (b) further comprises the steps of arranging the string of data pulses into a plurality of groups and storing each group in a predetermined address in the memory.

65. The method of claim 63 wherein the steps of arranging the data pulses in groups further comprises the steps of sequentially loading the data pulses into a register and transferring the group of data pulses in the register into a predetermined address in the memory when a predetermined number of data pulses are loaded into the register.

66. The method of claim 63 further comprising the steps of generating timing pulses at a predetermined constant rate and loading each data pulse into the register upon the occurrence of a timing pulse.

67. The method of claim 66 further comprising the steps of generating timing pulses at a predetermined constant rate;

counting the timing pulses;

generating a different address code when the count of timing pulses equals the number of data pulses comprising each data pulse group to provide a different address code for each group of data pulses.

68. The method of claim 63 further comprising the step of returning to the storing mode to repeat steps (b) through (d) upon the occurrence of the next frame sync pulse forming part of said second composite video signal.

69. The method of claim 63 wherein the first composite video signal is prerecorded into a medium and step (a) further comprises the step of reading out the first composite video signal from the recording medium preparatory to converting the image data signal of the composite video signal into a string of pulses.

70. The method of claim 63 further comprising the steps of:

extracting the synchronizing signals for both the first and second composite video signals; and initiating storage of the groups of pulses responsive to the first frame pulse and the presence of image data from the first video signal.

71. The method of claim 70 further comprising the steps of terminating the storing of groups of data signals upon the occurrence of the next framing pulse forming part of said first composite video signal; and thereafter reading each group of data pulses from storage responsive to a corresponding line sync pulse forming part of said second composite video signal.

72. The method of claim 71 further comprising the steps of:

terminating the reading out of the groups of data pulses from storage responsive to the next occurring frame sync pulse forming part of said second composite video signal.

73. The method of claim 63 wherein step (d) further comprises the steps of:

adding a predetermined signal level to said second composite video signal upon the occurrence of data pulses of a first binary state.

74. The method of claim 63 wherein step (d) further comprises the steps of:

replacing the portion of the second composite video signal occurring during the presence of a data pulse of a first binary state with a signal of a predetermined level.

75. The method of claim 74 wherein the level of the replacement signal is a medium gray level.

76. Apparatus for combining first and second composite video signals, each comprised of image data and frame and line sync pulses, comprising:

means for converting the image data of said first composite video signal into a string of binary pulses;

means for storing said string of pulses in groups of a predetermined number of pulses responsive to the occurrence of a frame sync pulse forming part of said first composite video signal;

means for reading out each group of stored pulses responsive to the next succeeding frame sync pulse forming part of said first composite video signal;

means for sequentially combining each pulse from a group of pulses read-out of the storing means with said second composite video signal.

77. The apparatus of claim 76 further comprising:

first means for extracting sync signals from said first composite video signal;

second means for extracting sync signals from said second composite video signal;

mode determining means for establishing a store mode responsive to a frame sync signal from said first extracting means;

timing pulse generating means;

said storing means including means responsive to line sync pulses and timing pulses from said timing pulse generating means for storing said groups of pulses;

means responsive to said store mode condition for applying line sync pulses from said first extracting means to said storing means.

78. The apparatus of claim 77 further comprising means responsive to the next frame sync pulse from said first extracting means occurring during the store mode for setting said mode determining means to establish a read mode condition; and means responsive to said read mode condition for applying line sync pulses from said second extracting means to said means for reading out.

79. The apparatus of claim 76 wherein said converting means comprises means for comparing said image data with a threshold level for converting portions of the image data into a signal of a first binary level when the data is above the threshold level and into a signal of a second binary level when the image data is below the threshold level.

80. The apparatus of claim 79 further comprising:

timing pulse generator means;

means responsive to a predetermined number of timing pulses for generating a group signal;

serial-to-parallel converter means having serial input means and parallel output means for shifting the binary state of the data at the input means into said converter means responsive to a timing pulse and for reading out a group of binary states from said parallel output means responsive to a group signal.

81. The apparatus of claim 80 further comprising: address generating means;
said storing means comprising memory means having a plurality of memeory locations, each capable of storing a group of data bits, each memory location being accessed by an address for either storage or retrieval;
address generating means for generating addresses responsive to said group pulses and the line sync pulses from said first retracting means during said store mode condition and for generating addresses from said group pulses and the line sync pulses from said second extracting means during a read mode condition.

82. The apparatus of claim 76 further comprising parallel-to-serial converting means having parallel input means and serial output means for receiving a stored group of data signals at said input means from said storing means responsive to a line sync pulse from said second extracting means and for serially steeping each data signal from said serial output means to said combining means responsive to said timing pulses.

83. Apparatus for generating a persistent image for superimposed display upon television monitor means with the image of a composite video signal having line and frame sync pulses and image data comprising:
memory means for storing groups of binary data representing an image to be combined with the composite video signal;
means for reading out said groups of data from said memory means responsive to said line sync signals;
means for sequentially combinding each data bit in each group of data with said composite video signal;
means for providing a start signal;
mode control means responsive to said start signal for producing an introductory mode condition;
means responsive to said introductory mode condition and said frame sync pulses for repetitively reading out said groups of data;
means for counting said frame sync pulses; and
means responsive to a predetermined count in said frame sync pulse counting means for terminating said introduction mode condition from said mode control means; and
means for disabling said means for repeatedly reading said groups of binary data to terminate the persistent image superimposed upon the image generated by the composite video signal.

84. The means of claim 83 wherein said mode control means comprises bistable circuit for establishing an introductory mode state responsive to a start signal; and
said counting means resetting said bistable circuit to a quiescent state upon reaching a predetermined count.

85. The means of claim 84 wherein said means for repeatedly reading out said groups of data signals comprises address counter means periodically advanced by said timing pulses for sequentially reading out each group of data signal; and
means for restarting said address counter means responsive to each frame sync pulse during said introductory mode condition.

86. The means of claim 85 wherein said restarting means further comprises gate means for generating a restart signal responsive to an introductory mode condition and a frame sync pulse;
said address counter means including an input for receiving said restart signal to return the address counter means to a count representing the first address of the groups of data signals representing the image to be combined with the composite video signal.

87. The means of claim 84 wherein said memory means comprises a plug-in memory and means for receiving said plug-in memory;
said means responsive to a start condition comprising means for setting said bistable circuit responsive to insertion of the plug-in memory into said memory receiving means.

88. Apparatus for generating a persistent image for superimposed display upon television monitor means with the image of a composite video signal line and frame sync pulses and image data comprising:
memory means for storing groups of binary data representing an image to be combined with the composite video signal;
means for reading out said groups of data from said memory means responsive to said line sync signals;
means for combining each data bit comprising said data group with said composite video signal in a serial fashion;
address counter means for generating addresses responsive to selected timing pulses for selectively extracting the groups of data signals from said memory means;
temporary storage means;
repeat counter means for storing a repeat count and including means for counting frame sync pulses and means for comparing the count in said frame sync pulse counting means with said repeat count;
temporary storage means;
repeat control means responsive to retrieval of a repeat control word stored in said memory means and comprised of a repeat instruction code portion and a repeat count for transferring an address from said address counter means to said temporary storing means;
said repeat control means further including means for transferring the repeat count into said repeat counter means responsive to said repeat instruction code; and
said repeat control means including means responsive to each frame sync pulse for transferring the address in said temporary storing means into said address counter means; and
said repeat counter means disabling said repeat control means when said frame sync pulse counting means reaches a predetermined count.

89. Means for periodically superimposing data upon a television receiver by periodically combining said data with a composite video signal being received by said receiver and being comprises of frame and line sync pulses and image data comprising:
a memory containing groups of binary data each stored in a predetermined storage location, said binary data comprising image information and function codes;
means for reading out said groups of data in a sequential manner;
means for combining the data groups with said composite video signal;
clock means for generating time information;

said clock means including means for comparing a start timed event count with said time information to generate a start signal;

means responsive to a retrieval of a function code containing a start timed event code from said memory means for transferring a timed event count to said clock means;

said comparison means initiating retrieval of a group of data representing the information to be displayed when said timing information compares with said timed event count to display the information to be displayed on the display means of the television receiver.

90. The means of claim 89 wherein said clock means further comprises means for generating time data.

91. The means of claim 90 wherein said time data represents at least time of day.

92. The means of claim 90 wherein said clock means time data represents time of day and date information.

93. The means of claim 83 wherein said read-out means comprises:
an address counter;
timing pulse means for periodically advancing said address counter;
said address counter means including reset means for resetting the count in said address counter means;
means for coupling said frame sync pulses to said reset means responsive to a introductory mode condition.

94. Means for generating pulses which are in synchronism with the sync pulses of a composite video signal comprised of frame and line sync signals and image information, comprising:
timing pulse generator means;
bistable means having a quiescent mode state and a counting mode state and being responsive to a line sync signal to assume said counting mode state;
timing pulse control means responsive to said counting mode state for restarting said timimg pulse generator means;
counter means responsive to said counting mode state for counting timing pulses, said counter means providing an output signal when a predetermined count of timing pulses have been accumulated to reset said bistable means to assume said quiescent state awaiting the next line sync signal;
said timing pulse control means disabling said timing pulse generating means responsive to the counter means output signal; and
said bistable means being set to the counting mode state only the occurrence of the next line sync pulse to enable said timing pulse control means to restart said timing pulse generator means.

95. The means of claim 94 further comprising:
second bistable means responsive to said quiescent condition and the presence of a vertical sync pulse from said composite video signal for generating a vertical sync condition.

96. The means of claim 95 wherein said counter means is provided with a count capacity sufficient to cause the output signal generated by said counter means responsive to said timing pulses occures during the latter portion of the vertical sync pulse derived from composite video signal to assure the presence of said vertical sync pulse.

97. The means of claim 97 wherein the latter portion of the vertical sync pulse comprises the latter half thereof.

98. A method for synchronizing the generation of timimg pulses generated by a timing pulse generator which sync pulses occur at predetermined intervals comprising the steps of:
blocking the opertion of said timing pulse generator;
unblocking the opertion of the timing pulse generator upon the occurrence of a sync pulse;
counting the number of timing pulses developed when the operation of the timing pulse generator is unblocked;
blocking the operation of the timing pulse generator when a predetermined number of timing pulses have been counted; and
restarting the timing pulse generator when the next sync pulse is detected.

99. The method of claim 98 wherein said predetermined number is sufficient to block the operation of the timing pulse generator just prior to the occurrence of the next timing pulse.

100. The method of claim 98 wherein the incoming signal contains a second sync pulse of greater duration than said first-mentioned sync pulse further comprising the steps of:
generating a second sync pulse signal when the second type sync pulse contained in the incoming signal is present after counting said predetermined number of timing pulses.

101. A method for generating timing pulses from a timing pulse generator which timing pulses are in synchronism with sync signals forming part of an incoming composite signal and in which a gate is coupled to said generator for blocking and unblocking the operation thereof and a bistable circuit having a blocking state and an unblocking state for respectively operating the gate to block or unblock the operation of said generator, comprising the steps of initially setting the latch to the blocking state;
setting the latch to the unblocking state upon the occurrence of the first sync pulse;
counting pulses developed by the generator;
setting the latch to the blocking state when a predetermined number of timing pulses have been counted, said predetermined number being chosen to set the latch to the blocking state just prior to receipt of the next occurring sync pulse; and
restarting the generator upon the occurrence of the next sync pulse.

102. The method of claim 101 further comprising the step of differentiating the first-mentioned sync pulse of said composite signal from a second sync pulse of a greater duration than said first-mentioned sync pulse and comprising the steps of:
examining the composite signal and generating a second sync pulse output responsive to the presence of the second sync pulse in the composite signal when the latch has been reset to the blocking state, said predetermined number of timing pulses being chosen so that the first-mentioned sync pulses are terminated before the predetermined count is reached and so that the second sync pulse is not terminated when the predetermined count is reached.

103. Apparatus for superimposing signals upon a composite video signal including at least frame and line synchronizing signals, said apparatus comprising:
vertical sync detecting means for generating an output responsive to each frame sync signal in said video signal;

line sync detecting means for generating an output responsive to each horizontal sync signal in said video signal;

memory means for storing variable data comprising selectable frame counts, selectable line counts, and a selectable data pattern;

means for generating timing pulse signals;

temporary storage means;

means for transferring a selected frame count to said temporary storage means from said memory responsive to a reset signal;

means for accumulating outputs from said vertical sync generating means responsive to said reset signal;

means for comparing the count in said accumulating means and said temporary storage means to generate a compare signal when said counts compare;

means for transferring a selected line count from said memory means responsive to said compare signal;

means for counting output signals from said line sync detector means;

said compare means comparing the line sync output signals counted with the present contents of said temporary storage means for generating a compare signal when said counts compare;

means for transferring a selected pulse count from said memory means to said temporary storage means responsive to said compare signal;

said selecting means including means for accumulating signals from said pulse generating means;

said comparing means generating a compare signal when the count in said means for accumulating signals compares with the count in said temporary storage means;

means for transferring a data work to said temporary storage means responsive to said compare signal; and means for attenuating the composite video signal at the selected locations according to the state of bits of the data word.

104. The apparatus of claim 103 wherein said data word further includes a count portion;

means for shifting each data bit of the data word in said temporary storage means to said attenuating means;

said comparing means comparing the count of timing pulses accumulated in said accumulating means with the count portion of said data word for generating a compare signal when the count in said accumulating means compares with the count in the count portion of said data word; and means for selecting the next word stored in memory responsive to said compare signal.

105. The apparatus of claim 104 further comprising means for advancing data bits from the data word last transferred to said temporary storage means at a rate controlled by said pulse generating means.

106. The apparatus of claim 105 further comprising shift register means;

said data word further comprising an identifying code portion including at least one data bit for identifying a data word;

means responsive to said identifying bit for enabling said shift register means to shift data bits of the data word from said shift register under the control of said pulse generating means for attenuating said video signal.

107. A method for combining first and second composite video signals each being comprised of frame and line sync signals and analog-type image data comprising the steps of:

(a) converting the image data signal of said first composite video signal into a string of binary data pulses;

(b) sequentially storing in a memory said string of data pulses as multi-bit binary words upon the occurrence of a frame sync pulse in said first composite video signal;

(c) sequentially selecting each word from memory and sequentially reading out the data pulses of each binary word from the memory upon the occurrence of the next succeeding frame sync pulse forming part of said first composite video signal; and (d) sequentially combining each stored data pulse with said second composite video signal responsive to the frame and line sync pulses of said second composite video signal.

108. A method for superimposing data upon a composite video signal comprised of frame and line sync signals and image signals, said method including the steps of:

storing in sequential fashion in a memory line words, line position words, data words, and frame words, said frame, line and line position words each including an instruction code portion identifying the nature of the word and a count portion, said data words each including an instruction portion, a count portion, and a data portion;

said words being stored in a predetermined order so that they have consecutive memory addresses whereby each frame word is followed by at least a one line word, each line word is followed by at least one line position word, and whereby each frame word, except for an initial frame word, follows a data word;

establishing an initial count and extracting the initial frame word from the memory address associated with said initial count;

generating timing pulses;

counting said timing pulses responsive to extraction of the initial frame word;

comparing the count of accumulated timing pulses with the count of said initial frame word;

incrementing the memory address count when the frame count compares with the count of frame sync signals accumulated;

selecting the memory word at the present memory address count;

counting line sync pulses responsive to the instruction code portion of the selected word in memory;

comparing the count portion of the selected word with the accumulated line sync pulses;

incrementing the memory address count when the count of line sync pulses and the word count portion compare;

selecting the word in memory stored at the incremented memory address count;

counting timing pulses responsive to the instruction code portion of the word selected from memory;

incrementing the memory address count when the number of timing pulses counted equals the count in the count portion of the selected memory word;

selecting the word in memory at the present address count;

counting timing pulses responsive to the count portion of the selected memory word;

sequentially combining the data in the data portion of the selected memory word with the composite video signal at a rate determined by said timing pulses; and incrementing the memory address count when the count of the selected memory word compares with the accumulated count of timing pulses.

109. The method of claim 108 wherein the step of storing line words further comprises the step of storing a plurality of line words in a predetermined order so that the addresses of the stored line words in ascending incremental order whereby the number of line words stored in sequential fashion are selected to represent the desired number of lines to receive data.

* * * * *